(12) United States Patent
Johnson et al.

(10) Patent No.: US 9,925,512 B2
(45) Date of Patent: *Mar. 27, 2018

(54) EQUIPMENT ASSEMBLY FOR AND METHOD OF PROCESSING PARTICLES

(71) Applicant: CRITITECH, INC., Lawrence, KS (US)

(72) Inventors: Greg S. Johnson, Wichita, KS (US); Bala Subramaniam, Lawrence, KS (US); Fenghui Niu, Lawrence, KS (US); Jahna C. Espinosa, Lawrence, KS (US); Charles J. Decedue, Lawrence, KS (US); Gary E. Clapp, Lawrence, KS (US); Jacob M. Sittenauer, Topeka, KS (US)

(73) Assignee: CritiTech, Inc., Lawrence, KS (US)

( * ) Notice: Subject to any disclaimer, the term of this patent is extended or adjusted under 35 U.S.C. 154(b) by 258 days.

This patent is subject to a terminal disclaimer.

(21) Appl. No.: 14/852,811

(22) Filed: Sep. 14, 2015

(65) Prior Publication Data

US 2015/0375153 A1 Dec. 31, 2015

Related U.S. Application Data

(63) Continuation-in-part of application No. 14/306,938, filed on Jun. 17, 2014, now Pat. No. 9,233,348, which
(Continued)

(51) Int. Cl.
*B01D 11/04* (2006.01)
*B01J 3/00* (2006.01)
(Continued)

(52) U.S. Cl.
CPC ............. *B01J 19/24* (2013.01); *A61K 9/1688* (2013.01); *B01D 9/0013* (2013.01); *B01D 9/0054* (2013.01); *B01D 29/661* (2013.01); *B01J 3/008* (2013.01); *B01J 4/002* (2013.01); *B01J 8/006* (2013.01); *B01J 2219/00051* (2013.01);
(Continued)

(58) Field of Classification Search
CPC ............ B01D 11/0203; B01D 11/0411; B01D 46/0023; B01D 46/0027; B01D 46/0068; B01D 29/0079; B01J 3/008; A61J 3/02
See application file for complete search history.

(56) References Cited

U.S. PATENT DOCUMENTS 3,283,803 A 11/1966 Phillips
4,881,722 A 11/1989 Koizumi
(Continued)

*Primary Examiner* — Katherine Zalasky
(74) *Attorney, Agent, or Firm* — Rick Matos; Innovar, L.L.C.

(57) ABSTRACT

An equipment assembly for preparing, harvesting and collecting particles is disclosed. The assembly comprises a tandem filter system with one or more high pressure filters, one or more low pressure filters and one or more collection vessel. Particles can be prepared, harvested and collected continuously, semi-continuously or in a batch-type operation. A tandem filter system and its method of use are also disclosed. Particles made with the assembly and according the instant methods are also disclosed. The assembly provides improved particle harvesting and collection over other systems and permits continuous particle formation, in particular by dispersion of a solute-containing process fluid within a supercritical anti-solvent.

22 Claims, 11 Drawing Sheets

Related U.S. Application Data is a continuation of application No. 13/911,700, filed on Jun. 6, 2013, now Pat. No. 8,778,181, application No. 14/852,811, filed on Sep. 14, 2015, which is a continuation-in-part of application No. PCT/US2014/028507, filed on Mar. 14, 2014, which is a continuation-in-part of application No. 13/911,700, filed on Jun. 6, 2013, now Pat. No. 8,778,181.

(60) Provisional application No. 61/783,682, filed on Mar. 14, 2013.

(51) Int. Cl.

| | |
|---|---|
| B01D 46/48 | (2006.01) |
| B01J 19/24 | (2006.01) |
| B01D 9/00 | (2006.01) |
| B01D 29/66 | (2006.01) |
| A61K 9/16 | (2006.01) |
| B01J 4/00 | (2006.01) |
| B01J 8/00 | (2006.01) |
| A61J 3/02 | (2006.01) |

(52) U.S. Cl.
CPC ............... *B01J 2219/00162* (2013.01); *B01J 2219/00164* (2013.01); *Y02P 20/544* (2015.11)

(56) References Cited

U.S. PATENT DOCUMENTS

| | | |
|---|---|---|
| 5,460,701 A | 10/1995 | Parker |
| 5,527,466 A | 6/1996 | Li |
| 5,571,299 A | 11/1996 | Tonn |
| 5,584,913 A | 12/1996 | Williams |
| 5,864,923 A | 2/1999 | Rouanet |
| 5,874,029 A | 2/1999 | Subramaniam |
| 5,874,684 A | 2/1999 | Parker |
| 5,961,835 A | 10/1999 | Sarrade |
| 5,981,474 A | 11/1999 | Manning |
| 6,113,795 A | 9/2000 | Subramaniam |
| 6,270,732 B1 | 8/2001 | Gardner |
| 6,440,337 B1 | 8/2002 | Hanna |
| 6,620,351 B2 | 9/2003 | Gupta |
| 6,830,717 B2 | 12/2004 | Avontuur |
| 6,860,907 B1 | 3/2005 | Hanna |
| 6,916,389 B2 | 7/2005 | Pesiri |
| 6,998,051 B2 | 2/2006 | Chattapadhyay |
| 7,150,766 B2 | 12/2006 | Hanna |
| 7,175,886 B2 | 2/2007 | Del Re |
| 7,250,152 B2 | 7/2007 | Gentile |
| 7,279,181 B2 | 10/2007 | Chattopadhyay |
| 7,291,296 B2 | 11/2007 | Perrut |
| 7,332,111 B2 | 2/2008 | Grothe |
| 7,449,136 B2 | 11/2008 | Skekunov |
| 7,455,797 B2 | 11/2008 | Shekunov |
| 7,635,442 B2 | 12/2009 | Del Re |
| 7,740,775 B2 | 6/2010 | Nicola |
| 8,215,486 B2 | 7/2012 | Roberts |
| 8,323,615 B2 | 12/2012 | Piran |
| 8,323,685 B2 | 12/2012 | Piran |
| 8,778,181 B1 | 7/2014 | Johnson |
| 9,233,348 B2 | 1/2016 | Johnson |
| 2001/0051118 A1 | 12/2001 | Mosso |
| 2002/0010982 A1 | 1/2002 | Hanna |
| 2013/0093111 A1 | 4/2013 | Demibuker |

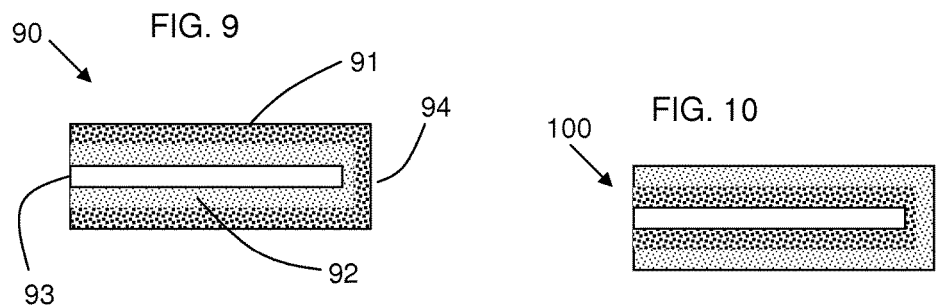
FIG. 9
FIG. 10
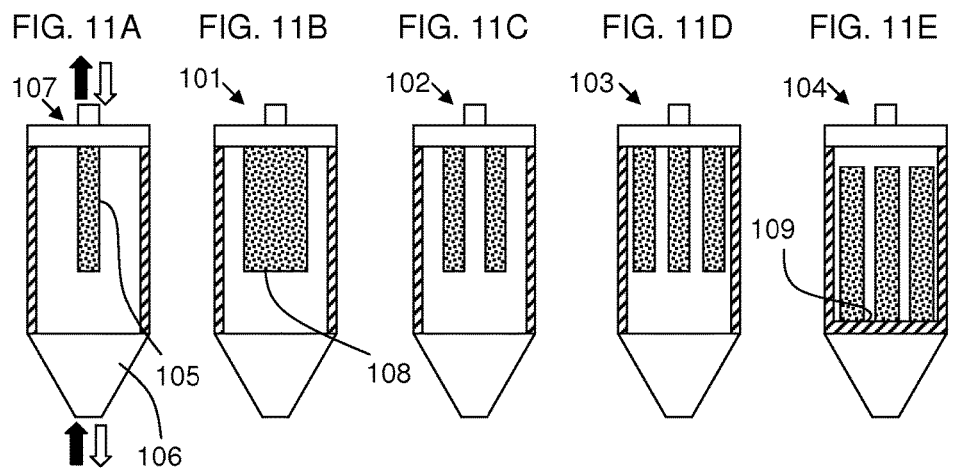
FIG. 11A  FIG. 11B  FIG. 11C  FIG. 11D  FIG. 11E
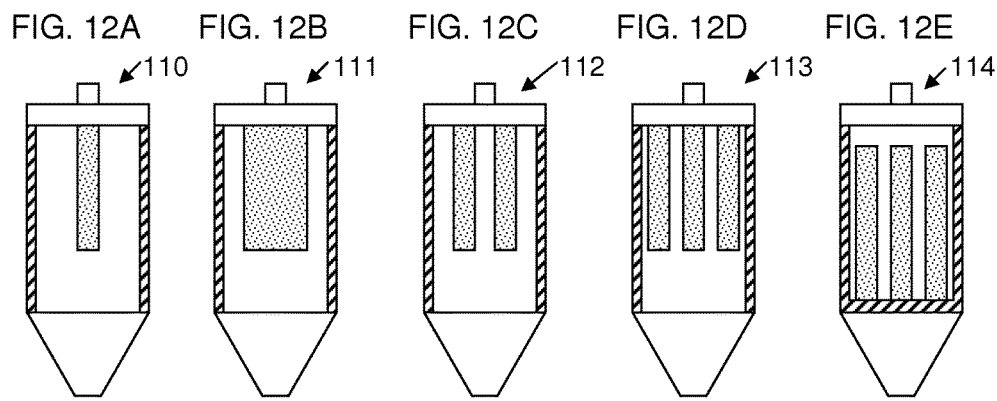
FIG. 12A  FIG. 12B  FIG. 12C  FIG. 12D  FIG. 12E

FIG. 13
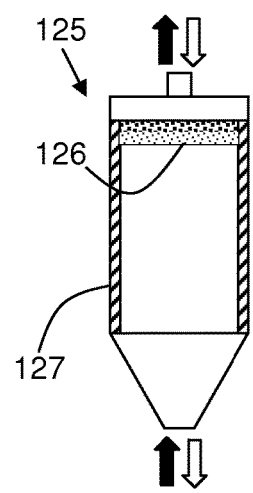
FIG. 14A  FIG. 14B
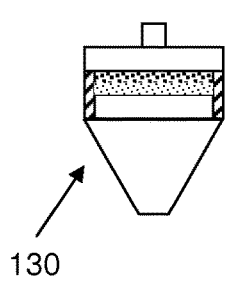 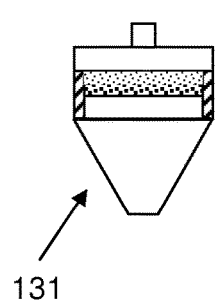
FIG. 15A  FIG. 15B
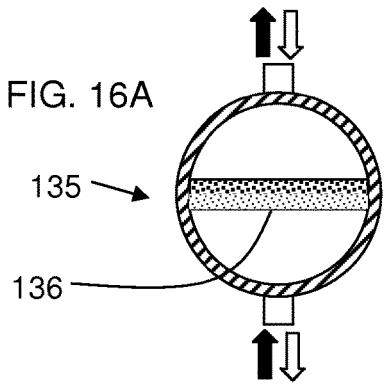
FIG. 16A
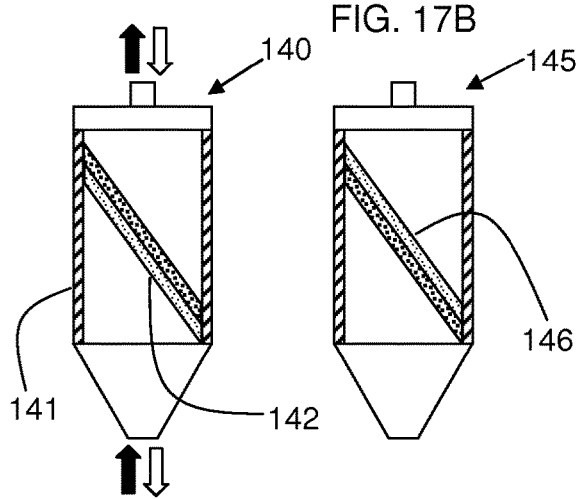
FIG. 17A  FIG. 17B
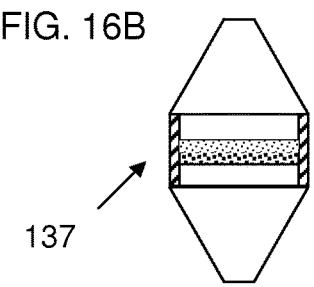
FIG. 16B

EQUIPMENT ASSEMBLY FOR AND METHOD OF PROCESSING PARTICLES

CROSS-REFERENCE TO EARLIER-FILED APPLICATION

The present application claims the benefit of and is a continuation-in-part of PCT/US2014/028507 filed Mar. 14, 2014, which claims the benefit of and is a continuation-in-part of U.S. Ser. No. 13/911,700, filed Jun. 6, 2013, now U.S. Pat. No. 8,778,181, issued Jul. 15, 2014, which claims the benefit of U.S. 61/783,682, filed Mar. 14, 2013, the entire disclosures of which are hereby incorporated by reference. The present application also claims the benefit of and is a continuation-in-part of U.S. Ser. No. 14/306,938, filed Jun. 17, 2014, which claims the benefit of and is a continuation of U.S. Ser. No. 13/911,700, filed Jun. 6, 2013, now U.S. Pat. No. 8,778,181, issued Jul. 15, 2014, which claims the benefit of U.S. 61/783,682, filed Mar. 14, 2013, the entire disclosures of which are hereby incorporated by reference

FIELD OF THE INVENTION

The present invention concerns an apparatus for processing particles. More particularly, the invention concerns a tandem filtration system for processing particles suspended in supercritical fluid. Methods for processing the particles to remove contaminants or to classify them are also provided.

BACKGROUND OF THE INVENTION

Particles can be prepared by adding a solubilized compound, i.e. a compound dissolved in one or more solvents, to an anti-solvent. Such a process can be used to prepare particles in many different size distributions. A key drawback of such a process, however, is the entrapment of solvent and/or anti-solvent within and/or on the surface of the particles.

Removal of solvent from the particles typically involves washing of the particles with additional amounts of anti-solvent, which unfortunately results in saturation of the particles with anti-solvent, unless the anti-solvent is very volatile. For this reason, supercritical fluid (SCF) is often employed as the anti-solvent. SCF, in particular supercritical carbon dioxide, is very volatile and easily removed from the particles. Solvents, however, are less volatile than the SCF and thus are more difficult to remove.

Due to the extreme volatility of supercritical carbon dioxide, it is a challenge to effectively harvest particles from it unless the particles are first physically separated from it. Filtration is the most common approach used for affecting separation of particles from SCF while still permitting repeated wash cycles. When microparticles or nanoparticles are being processed, however, it is more difficult to separate the particles from the SCF due to fouling of filters, and it is difficult to unfoul filters when a process is running. Moreover, typical filters used to separate the particles are flat dead-end filters, which must be opened to harvest the particles. These challenges make continuous processing and harvesting of particles extremely difficult to achieve.

Numerous such processes and apparatuses for the processing of drug, mineral, metal or toner particles in supercritical fluid have been disclosed: U.S. Pat. Nos. 6,270,732, 5,584,913, 5,571,299, 5,460,701, 4,881,722, 5,874,029, 5,874,684, 6,113,795, 5,961,835, 5,527,466, 7,740,775, 7,635,442, 7,175,886, 7,250,152, 7,279,181, 7,449,136, 6,916,389, 7,291,296, 7,332,111, 7,150,766, 6,860,907, 6,440,337, 6,830,714, 6,620,351, 5,981,474, 8,323,685, 8,323,615, 8,215,489, 6,998,051, 5,864,923, 7,455,797, U.S. 20020010982, and U.S. 20010051118. These systems typically employ dead-end filters, cyclones, bag filters, depth filters or other such types. Many of these systems cannot be operated continually since they require halting of operations and opening of components in the process stream in order to remove particles. An important aspect of supercritical fluid based processes is that supercritical pressure and temperature must be maintained throughout the filtration step to avoid phase separation of solvent from the SCF and avoid redissolution of the solute back into the solvent. This is particularly difficult to achieve when particle formation is conducted continuously.

A need remains for improved equipment and processes for the preparation, harvesting and collection of small particles, especially those prepared in SCF. In particular, there remains a need for a higher throughput system that can be operated continuously or semi-continuously and that permits particle collection with minimal or no cessation of the particle formation step.

SUMMARY OF THE INVENTION

The present invention seeks to overcome some or all of the disadvantages inherent in the art. The present invention provides an equipment assembly suitable for the preparation, harvesting and collection of particles. The invention is particularly suitable for processes employing solvent/anti-solvent formation of particles, especially of microparticles and nanoparticles. The invention employs a tandem filtration system comprising at least one high-pressure filter, at least one low pressure filter and at least one collection vessel. The tandem filtration system is placed downstream of a precipitation chamber in which particles are formed.

During operation, a precipitation fluid (comprising an anti-solvent for at least one solute) is charged into a precipitation chamber. A process fluid (comprising at least one solute dissolved in at least one solvent) is dispersed as droplets into the precipitation fluid, such that solvent diffuses away from droplets of process fluid and into the precipitation fluid, whereby the solute precipitates in the anti-solvent. The particle-containing precipitation milieu is conducted from the precipitation chamber to a high pressure harvesting filter, whereby the solvent/anti-solvent mixture is separated from the particles that accumulate at the surface of a porous element in the harvesting filter. A charge of clean anti-solvent is then flowed through the harvesting filter in the same direction as the precipitation milieu in order to remove residual solvent from the particles. The internal pressure of the harvesting filter is thereafter reduced and a low pressure gas is passed through the filter in the reverse direction of the precipitation milieu, thereby dislodging particles from the surface of the porous element. The gas conducts the particles to a low pressure collection filter, whereby the gas is separated from the particles at the surface of a porous element in the collection filter. The particles then fall due to (are assisted or forced by) gravity into a collection vessel.

The tandem filter system of the invention can be used to collect particles and even to wash/rinse particles, if desired to remove unwanted component(s) from the particles. A harvesting filter can be used to extract compounds from particles by extraction, to remove contaminants from particles by repeated washing, or to remove solvent from the particles. The filter can be used for, among other things, washing particles with and harvesting particles from antisolvent, especially supercritical anti-solvent. Accordingly, the unwanted component(s) in the particles will be soluble in the anti-solvent.

An aspect of the invention provides a high pressure particle harvesting filter system comprising:
a high pressure housing defining a lengthwise process cavity comprising a downwardly-pointing conical (tapered) portion, at least one inlet port and at least one outlet port;
a liquid particle suspension supply line engaged with the inlet port and configured to provide a high pressure liquid particle suspension comprising particles and anti-solvent;
a gas supply line engaged with the outlet port and configured to provide a low-pressure inert gas;
a temperature controller for controlling the temperature of the housing; and
at least one lengthwise porous element extending into the cavity and comprising a porous wall defining a lengthwise inner conduit conductively engaged with the at least one outlet port,
wherein,
the porous element is conductively engaged directly or indirectly with the outlet port;
the filter system is configured to receive high pressure particle suspension in a first forward process direction and to receive a low pressure inert gas in a second reverse process direction, wherein process direction is with respect to flow through the porous element.

Some embodiments of the invention include those wherein: 1) the harvesting filter system further comprises a collection vessel; 2) the collection vessel is vented; 3) the process cavity is vertically oriented along its lengthwise axis; 3) vertical orientation is perpendicular to the ground or parallel to the linear axis of a plumb bob line; 4) at least one inlet port is configured to serve as an outlet port for a gaseous particle suspension; 5) the porous element and the housing are cylindrical; 6) the temperature controller comprises a heating and/or cooling jacket surrounding the housing; 7) the geometry of the conical portion is such that the upper wider end has a diameter of about 25 to about 125 mm, the lower narrower end has a diameter of about 5 to about 50 mm and the conical portion is about 50 to about 250 mm in length; 8) the process cavity further comprises a linear cylindrical portion in which the porous element is disposed; 9) the spacing between the outer surface of the porous element and the inner surface of the process cavity is in the range of about 5 to about 100 mm, about 20 to about 100 mm, about 40 to about 100 mm, about 60 to 80 mm, about 70 mm; 10) the outlet port is configured as reversible-flow port, e.g. to serve as an outlet for liquid and an inlet for gas; 11) the diameter of the inner conduit is in the range of about 5 to about 60 mm, about 10 to about 50 mm, about 15 to about 35 mm, about 20 to 30 mm, about 25 mm; 12) the outer diameter of the porous element is in the range of about 10 to about 60 mm, about 15 to about 35 mm, about 20 to 30 mm, about 25 mm; 13) the liquid particle suspension comprises particles, antisolvent and solvent; 14) the system further comprises one or more valves that direct flow of a liquid particle suspension to the harvesting filter and direct flow of a gaseous particle suspension from the harvesting filter; and/or 15) a portion of the process cavity of the filter housing is cylindrical, rectangular, ellipsoidal or spherical. The porous element can be disposed within the process cavity such that its surface is tangential to, perpendicular to or at a non-perpendicular angle (1-89°, 20-80°, 30-60°, about 30°, about 45° or about 60°) with respect to the linear axis of the cavity or with respect to the overall flow of fluid across or through the surface of the porous element.

Another aspect of the invention provides a low pressure particle collection filter system comprising:
a low pressure housing defining a lengthwise process cavity and comprising at least one inlet port, at least one gas outlet port and at least one particle outlet port; and
a gaseous particle suspension supply line engaged with the at least one inlet and configured to provide a low pressure gaseous particle suspension comprising particles and gas;
at least one lengthwise porous element extending into the cavity and comprising a porous wall defining a lengthwise inner conduit conductively engaged with the at least one inlet port and the at least one particle outlet port;
wherein, the filter system is configured to receive low pressure gaseous particle suspension in a forward process direction;

the porous element is configured to retain particles and allow passage of gas to the at least one gas outlet;

the conduit of the porous element is oriented such that particles fall via gravity through the at least one particle outlet port.

Some embodiments of the invention include those wherein: 1) the system further comprises a particle collection vessel; 2) the collection vessel is vented; 3) the inner conduit is vertically oriented along its lengthwise axis; 4) vertical orientation is perpendicular to the ground or parallel to the linear axis of a plumb bob line; 5) at least one inlet port is configured to receive a gaseous particle suspension; 6) the porous element is cylindrical; 7) the inner conduit of the porous element has an inner diameter in the range of about 5 to about 60 mm, about 10 to about 50 mm, about 15 to about 35 mm, about 20 to 30 mm, about 25 mm; 8) the system further comprises a gas pulsing system configured to pulse gas (in a reverse operations direction) from the gas outlet of the housing to the porous element; 9) the collection vessel is disposed beneath the porous element or at a level below the porous element; 10) the vent of the collection vessel comprises filtration medium; 11) the system further comprises one or more valves upstream of the inlet port to direct the flow of a gaseous particle suspension into the collection filter; and/or 12) the system further comprises one or more valves downstream of the outlet port.

In some embodiments, the porous element: a) comprises substantially the same porosity throughout; b) comprises a first porous portion and a second porous portion, wherein the average diameter of the pores of the first portion is greater than the average diameter of the pores of the second portion; and/or c) comprises two substantially coextensive porous portions differing in the average diameter of their respective pores. In some embodiment, a first porous portion has an average pore diameter of about 0.3-0.6 microns, and a second porous portion has an average pore diameter of about 0.02-0.10 microns. The porous element can be a tube or plate. In some embodiments, a portion is a lamina and the porous element comprises two or more laminas.

In some embodiments, the high pressure filter comprises one or plural, e.g. two, three, four or more, porous elements. In some embodiments, the porous element is conductively engage with the upper portion of the filter assembly. In other embodiments, the porous element is conductively engaged with the lower portion of the filter assembly. One or more porous elements can together occupy up to about 90%, about 50%, about 25%, or about 10% of the volume of the process cavity of the filter assembly.

Another aspect of the invention comprises a particle formation and collection equipment assembly comprising:

a) a high pressure particle formation system comprising a pressurizable precipitation chamber comprising a SCF inlet, a process fluid inlet, a fluid outlet, a process fluid disperser configured to disperse process fluid into the chamber, wherein the system is configured to form a particle-containing high pressure liquid suspension; and b) a tandem filtration particle collection system comprising:
  1) at least one high pressure harvesting filter that receives a particle-containing high pressure liquid suspension from the particle formation system and to form a particle-containing low pressure gaseous suspension,
  2) at least one low pressure collection filter in tandem to the harvesting filter that receives a particle-containing low pressure gaseous suspension from the harvesting filter, to separate gas from particles and to conduct particles to a collection vessel, and
  3) at least one collection vessel that receives and collect particles.

Another aspect of the invention comprises a particle formation and collection equipment assembly comprising:

a) a high pressure particle formation system that forms a particle-containing high pressure liquid suspension;
b) at least one high pressure harvesting filter system that receives and filters the particle-containing high pressure liquid suspension from the particle formation system and forms a particle-containing low pressure gaseous suspension;
c) at least one collection vessel system, downstream of the harvesting filter, comprising at least one particle inlet that receives the particle-containing low pressure gaseous suspension from the harvesting filter and at least one gas outlet; and
d) at least one low pressure collection filter system, conductively engaged with the at least one gas outlet and downstream of the at least one collection vessel, that separates gas from particles in the particle-containing low pressure gaseous suspension and retains particles in the collection vessel.

Another aspect of the invention comprises a particle formation and collection equipment assembly comprising:
a) a high pressure particle formation system that forms a particle-containing high pressure liquid suspension;
b) at least one high pressure harvesting filter system that receives and filters the particle-containing high pressure liquid suspension from the particle formation system and forms a particle-containing low pressure gaseous suspension;
c) at least one collection vessel system, downstream of the harvesting filter, that receives the particle-containing low pressure gaseous suspension from the harvesting filter and collects particles; and
d) at least one low pressure collection filter system, conductively engaged with and downstream of the at least one collection vessel, that separates gas from particles in the particle-containing low pressure gaseous suspension and retains particles in the collection vessel.

Some embodiments of the invention include those wherein: 1) a majority of gas exits the collection system through one or more collection filters engaged with one or more gas outlets of the collection system; 2) the collection system comprises at least one collection vessel, at least one removable header (cover), at least one particle inlet, and at least one gas outlet; 3) the collection filter and harvesting filter are disposed above the collection system; 4) at least a portion of filtration medium of the collection filter is disposed within a cavity defined by the header and collection vessel; 5) the collection system further comprises at least one vent and/or at least one sampling port; 6) the collection filter comprises at least one porous element that extends into the collection system, wherein the porous element comprises a lumen (conduit) defined by filtration media, wherein the conduit has a closed end and an open end; 7) the collection system comprises a header and a collection vessel that are detachable from one another; 8) the porous element can be sintered or fritted or can be a cloth or mesh or wound fiber or as otherwise described herein; 9) the porous element is a flat or curved plate; 9) the collection system comprises at least one particle inlet, at least one gas outlet, and an extended header (cover) and a collection vessel that are detachable from one another and together form a receptacle (cavity) for particles that are collected; 10) the particle inlet of the collection system is engaged with a horizontally offset conduit that conducts the gaseous particle suspension (from the harvesting filter system) into the collection system; 11) the collection vessel is removable; 12) the collection filter system further comprises a gas inlet for gas used to back-flush the filtration medium of the collection filter(s), thereby removing (dislodging) any particles that have accumulated on its exposed surface within the collection vessel; 13) the collection filter is engaged with and disposed above the gas outlet of the collection system and the porous element (filtration medium) of the collection filter is not disposed within the cavity defined by the header and vessel of the collection system; and/or 14) the collection filter system further comprises a gas inlet used to back-flush gas through filtration medium of the collection filter.

Another aspect of the invention provides a process for filtering and collecting particles from a supercritical fluid or near-supercritical fluid particle suspension, the process comprising: a) filtering the supercritical fluid or near supercritical fluid particle suspension in a first process direction through filtration medium of a high pressure harvesting filter; b) reducing the pressure of the atmosphere within the harvesting filter; c) flowing a low pressure gas in an opposite second process direction through the filtration medium of the harvesting filter to form a gaseous particle suspension which is conducted into a collection system via a particle inlet thereof; and d) filtering the low pressure gaseous particle suspension through filtration medium of a collection filter engaged with a gas outlet of the collection system, thereby retaining and collecting particles within the collection system.

Another aspect of the invention comprises a particle formation and collection equipment assembly comprising:
a) a SCF supply system;
b) a process fluid supply system;
c) at least one particle formation system comprising a pressurizable precipitation chamber comprising a SCF inlet, a process fluid inlet, a fluid outlet, a process fluid disperser configured to disperse process fluid into the chamber; and
d) at least one tandem filter particle filtration system connected to the particle formation system and comprising at least one high pressure harvesting filter and at least one low pressure collection filter, wherein the collection filter is downstream of the harvesting filter; and
e) at least one collection system connected to the particle filtration system and comprising at least one collection vessel.

Some embodiments of the invention include those wherein: 1) the disperser comprises a vibratable member; 2) the vibratable member is a nozzle, plate or mesh; 3) the disperser comprises a vibrator comprising at least one piezoelectric component; 4) the disperser comprises a conduit for process fluid and a conduit for SCF; 5) the disperser comprises a vibrator and a vibratable member; 6) the disperser comprises a vibrator and a nozzle, plate or mesh; 7) the equipment assembly comprises at least two tandem filter particle filtration systems; 8) the at least two tandem filter particle filtration systems are arranged in parallel and are configured to operate alternately; 9) the at least two tandem filter particle filtration systems are arranged in parallel and are configured to operate simultaneously; 10) the equipment assembly comprises at least two collection systems; 11) the disperser comprises a converging or diverging nozzle that generates a standing ultrasonic wave during operation; 12) the system further comprises one or more valves, one or more actuators, one or more back pressure regulators and/or one or more flow controllers; 13) the system further comprises software or logic to control operation of one or more valves, one or more actuators, one or more back pressure regulators and/or one or more flow controllers; 14) the disperser comprises a capillary nozzle; and/or 15) the system further comprises one or more computers having a memory storage medium containing software or logic adapted to control operation of one or more components of the system.

Another aspect of the invention provides a method of processing a suspension of particles, the method comprising:
a) providing a tandem filter equipment assembly comprising: 1) at least one high pressure harvesting filter; 2) at least one low pressure collection filter; and 3) at least one collection vessel;
b) providing a SCF liquid suspension of particles;
c) filtering the SCF liquid suspension by flowing it through the harvesting filter in a forward direction to retain particles in the filter;
d) removing particles from the harvesting filter by flowing low pressure gas through the harvesting filter in a reverse direction and conducting the particles as a gaseous suspension to a low pressure collection filter;
e) separating the particles from gas by flowing the gaseous suspension through the collection filter in a forward direction; and
f) conducting the particles to and collecting the particles in a collection vessel.

In some aspects, the invention provides a powder made according to a process of the invention or a powder made with a system of the invention.

Some embodiments of the invention include those wherein: 1) the harvesting filter is a high pressure filter; 2) the process further comprises charging clean (not containing solvent or particles) SCF liquid into the harvesting filter in a forward direction; 3) the process further comprises reducing the internal pressure of the harvesting filter; 4) the process comprises forcing the particles by gravity to the collection vessel; 5) the high pressure filter and precipitation chamber are adapted to operate at about 800 to about 3000 psi, about 1000 to about 2000 psi, or about 1,110 to about 1,400 psi; and/or 6) a combination thereof.

The equipment assembly can further comprise: a) one or more particle harvesting filters; b) one or more particle collection filters; c) one or more vented collection vessels; d) one or more pressure sensors; e) one or more temperature sensors; 0 one or more temperature controllers at least partially surrounding one or more of the precipitation chamber, collection filter, emptying filter and collection vessel; g) one or more heaters for $scCO_2$; h) one or more pumps for pumping process fluid and/or $scCO_2$; i) one or more solvent separation vessels; j) one or more solvent collection vessels; k) the system comprises one or more in-line sensors; l) an in-line sensor can be selected from the group consisting of a spectrophotometric sensor, particle size sensor, pressure sensor, temperature sensor, infrared sensor, near-infrared sensor, and ultraviolet sensor; or k) any combination thereof.

Some embodiments of the invention include those wherein: a) the equipment assembly comprises two particle harvesting filters, two particle collection filters and two collection vessels; b) the equipment assembly comprises two particle harvesting filters, one particle collection filter and one or more collection vessels; c) the equipment assembly comprises two particle harvesting filters, two particle collection filters and one or more collection vessels; d) the equipment assembly comprises two particle harvesting filters, one particle collection filter and one or more collection vessels; e) the equipment assembly comprises two tandem filter particle harvesting and collection systems arranged in parallel; f) the equipment assembly comprises two or more particle harvesting filters arranged in parallel, one particle collection filter and two or more collection vessels arranged in parallel; g) the equipment assembly comprises two or more precipitation chambers; or h) any combination thereof.

The invention includes all combinations of the aspects, embodiments and sb-embodiments disclosed herein.

BRIEF DESCRIPTION OF THE FIGURES

The following figures form part of the present description and describe exemplary embodiments of the claimed invention. The skilled artisan will be able to practice the invention without undue experimentation in light of these figures and the description herein.

FIG. 9 depicts a cross-sectional side view of an exemplary embodiment of a porous element.

FIG. 10 depicts a cross-sectional side view of another exemplary embodiment of a porous element.

FIGS. 11A-11E depict partial sectional side views of exemplary high pressure filters employing the porous element of FIG. 9.

FIGS. 12A-12E depict partial sectional side views of exemplary high pressure filters employing the porous element of FIG. 10.

FIG. 13 depicts a sectional side view of an exemplary porous element in the shape of a flat plate.

FIGS. 14A, 14B, 15A, 15B, 16A, 16B, 17A and 17B depict partial sectional side views of exemplary high pressure filters employing the porous element of FIG. 13.

DETAILED DESCRIPTION OF THE INVENTION

Aspects and embodiments of the invention include a particle formation, separation and collection system, a tandem filter particle separation and collection system, a high pressure harvesting filter, a low pressure collection filter, a method of forming, separating and collecting particles, and a method of treating particles. The collection system can be placed between the harvesting filter and the collection filter, wherein placement of the collection system is with respect to the flow of particles through the equipment assembly.

Figure 1:
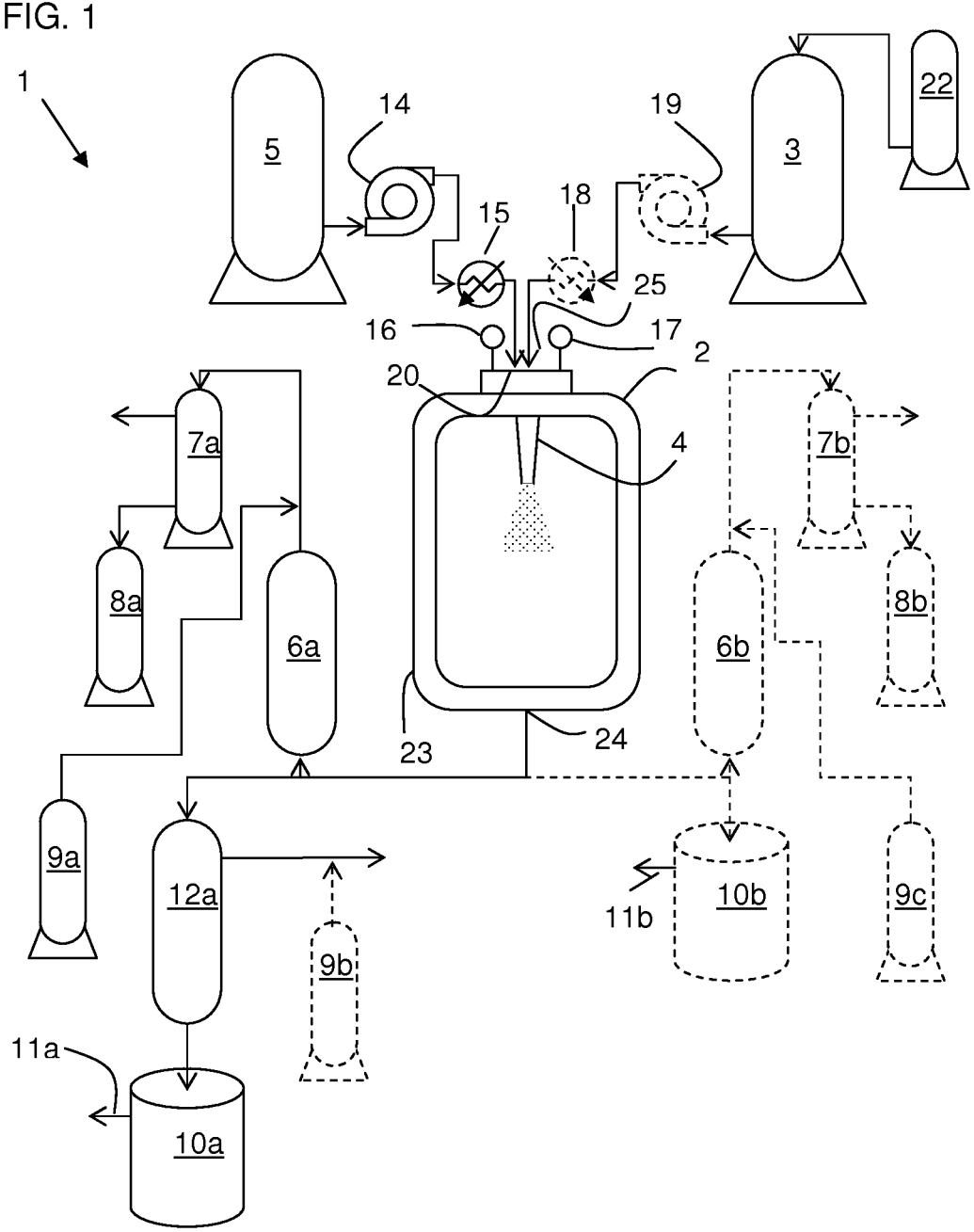
FIG. 1 depicts an exemplary particle formation, separation and collection system (1) of the invention comprising an exemplary tandem filter particle filtration system or a single-filter particle filtration system.

The equipment assembly (1, schematic in FIG. 1) is used to prepare particles by precipitation of a solute from a solute-containing process fluid dispersed into anti-solvent. The process fluid from a process fluid supply system (3) enters the nozzle (4) via an inlet (25) of the precipitation chamber (2). At the same time, anti-solvent from an anti-solvent supply system (5) is flowed through the nozzle, whereby the process fluid and anti-solvent are intimately mixed causing dispersion of the process fluid into the anti-solvent. Alternatively, the anti-solvent is charged into the precipitation chamber via a separate inlet and process fluid is dispersed therein by way of the nozzle. Upon contact of the droplets of process fluid with anti-solvent, solvent in the process fluid diffuses into the anti-solvent and causes precipitation of the solute into particles. The particles are then separated from the anti-solvent/solvent mixture by way of at least one filter.

Following formation of the particles in the precipitation chamber, the precipitation fluid milieu (a liquid particle suspension comprising $scCO_2$, solvent and particles) is conducted through an outlet (24) to at least one particle harvesting filter (6a) comprising a housing, an inlet, an outlet and an interior porous element engaged to the outlet, wherein the fluid $scCO_2$ and solvent are separated from the particles at the surface of the porous element. The $scCO_2$ and solvent pass through the porous element and are conducted to a solvent separation vessel (7a). From there, the separated solvent is conducted to a solvent collection vessel (8a). Placement of the outlet (24) is such that it will minimize accumulation of the precipitation fluid milieu in one or more regions within the chamber when process is being conducted as a flow-through process. For example, if the nozzle is at one end of the housing, the anti-solvent inlet will be disposed at or toward the same end of the housing and the outlet will be disposed at or toward the opposite end of the housing.

The particles are then discharged from the harvesting filter. This is accomplished by providing stopping the flow of $scCO_2$ into the harvesting filter, reducing the internal pressure of the harvesting filter and passing a reverse flow of gas, e.g. inert gas from a supply (9a), across the porous element to dislodge the particles from the porous element. The dislodged particles are conducted through to at least one particle collection filter (12a) comprising a housing, an inlet, an outlet and an interior porous element engaged to the outlet, wherein the gas is separated from the particles at the interior or exterior surface of the porous element. As the particles separate, they are discharged by gravity into the collection vessel (10a). Alternatively or in addition, particles can be removed from the collection filter by providing a reverse flow of gas, such as from a supply (9b), across the porous element to dislodge the particles from the porous element. The dislodged particles can be collected in a collection vessel (10a) equipped with a vent. A collection vessel can be placed beneath the harvesting filter and/or the collection filter. The collection filter and associated equipment are optional. In this case, the alternate embodiment in FIG. 1 (depicted in hashed lines) is employed.

The gas used to dislodge particles from the porous element can be any gaseous material. It is preferably an inert non-toxic gas. Suitable gases include nitrogen, helium, argon, or carbon dioxide.

Since the anti-solvent can be provided as a supercritical fluid, the equipment assembly can further comprise a pump (14) and heater (15). The order of placement of the pump and heater can be reversed if needed. Any pump capable of raising the internal pressure of the equipment assembly to a near critical or to the supercritical pressure of the anti-solvent can be used. In some embodiments, the pump is capable of pressurizing the precipitation chamber to a pressure of about 800 to about 3000 psi. In some embodiments, the pump used to pressurize the anti-solvent or process fluid is a metering pump. Likewise, any heater capable of raising the temperature of the anti-solvent to its near critical temperature or to its supercritical temperature can be used. The heater is independently upon each occurrence selected from a flow through heater placed in a conduit or a heating element coupled to a respective supply system of solvent or process fluid. In some embodiments, the heater is capable of heating the process fluid or anti-solvent to a temperature of about 30° to about 70° C.

Although not indicated in some of the drawings, the equipment assembly further comprises plural valves that control the flow of process fluid, anti-solvent, gas, and precipitation fluid milieu. The assembly also comprises one or more flow restrictors (back-pressure regulators) used to regulate the flow of fluid and/or gas through, and thus to regulate the pressure in, the various components of the assembly. These components are used to regulate temperature, flow rate of suspension (liquid or gas) and the internal pressure of individual components of the assembly. In some embodiments, a controller is adapted to maintain the internal pressure of a component to within about ±10%, about ±5%, or about ±1% of a pre-set value. In some embodiments, a controller is adapted to maintain the internal temperature of a component to within about ±10°, about ±5° or about ±2° C. of a pre-set value. In some embodiments, a controller is adapted to maintain the flow rate of supercritical fluid, liquid particle suspension, gas or gaseous particle suspension of a component to within about ±10-33% of a pre-set value. In some embodiments, a controller is adapted to maintain the flow rate of process fluid to a component to within about ±5%, about ±2.5%, about ±1% or about ±0.5% of a pre-set value.

The process fluid is optionally heated via a heater (18), and/or it can be pressurized with a pump (19) or with a pressurized gas, i.e. from a supply (22). The pressure of the process fluid entering the precipitation chamber should be greater than the pressure of the precipitation chamber to ensure positive (forward) flow of the process fluid through the vibrating mesh. The difference in pressure (pressure differential in favor of the process fluid) can be adjusted as desired, keeping in mind that, in general, the greater the pressure differential the faster the flow of process fluid through the vibrating mesh. The pressure differential will generally be at least 5 psi or in the range of about 1 to about 200, about 1 to about 50 or about 1 about 10 psi. The pressure within the chamber can be monitored with a pressure sensor (16). This pressure differential can be used with other dispersers and equipment assemblies described herein.

Control of the pressure, temperature, flow rate of solvent and choice of solvent differential can be used to manipulate particle properties. The rate of desolvation of solutes in solution can alter particle properties such as mean particle diameter, particle size distribution, crystal shape and degree of crystallinity. By carefully controlling the pressure of the anti-solvent compressed gas the rate of desolvation can be increased or decreased to affect particle size. Similarly, changes in the temperature, solvent and ratio of solution to anti-solvent each can alter the rate at which crystals form and therefore alter the properties of the resultant crystals or particles. The particles can be crystalline, amorphous or a combination thereof.

The precipitation chamber can be equipped with a temperature controller (23), which can either heat or cool the chamber as needed, in order to maintain the temperature within the chamber at or above the critical temperature of the anti-solvent. The temperature within the chamber can be monitored with a temperature sensor (17). The temperature controller is depicted as being a heating and/or cooling jacket that surrounds at least a portion of the housing defining the chamber. A heating and/or cooling element can optionally be disposed within the chamber or built into the wall of the housing.

The temperature controller can be exterior to, interior to or integral with the housing. In some embodiments, the temperature controller jackets the housing. It can comprise at least one heating element, at least one cooling element or a combination thereof. The jacket can comprise a gas, vapor, steam or fluid-filled cavity. In some embodiments, the housing comprises an interior wall defining the process cavity and an exterior wall spaced away from the interior wall, wherein the walls and the space there between together define a temperature-controlling jacket.

The collection vessel (10) can be placed as desired in the equipment assembly. It can be located beneath or at a level below a respective filter. The particles in a respective filter can be conducted into the collection vessel via gravity and/or a gas, as described herein or by mechanical equipment. It has been discovered that the collection vessel should be vented (11) in order to maximize collection of particles. The vent (11) can include a frit, cloth, bag or other porous element to retain the particles while permitting passage of the gas.

FIG. 2 depicts a schematic of an alternate equipment assembly (25) that can be used to prepare, harvest and collect particles. The anti-solvent supply system and process fluid supply system are similar to those of FIG. 1; however, the precipitation chamber comprises a first inlet (25) for process fluid and a separate second inlet (21*a*) for anti-solvent. The second inlet is located adjacent an atomizer (27) that disperses the process fluid as droplets into the precipitation chamber. Clean anti-solvent enters the precipitation chamber via an inlet (21*a*) at a location that is near the atomizer to aid in removal of the solvent/anti-solvent/precipitate mixture that has formed in proximity of the atomizer. Alternatively, the inlet (21*b*) for clean anti-solvent can be located within the same section, e.g. same half, third, quarter, fifth or smaller fraction thereof, of the chamber as the atomizer. It is only important that clean anti-solvent enter the chamber at a location sufficiently close to the atomizer to facilitate rapid removal of fluid mixture containing solvent/anti-solvent/precipitate (precipitation milieu) away from the proximity of the atomizer.

The flow rate of anti-solvent into the chamber will exceed the flow rate of process fluid, via the atomizer, into the chamber. Doing so will minimize accumulation of excessively high concentration of solvent in the precipitation fluid milieu, in particular in the region of atomization. The ratio of flow rate (l/min) of anti-solvent to flow rate (l/min) of solvent will generally be at least 50:1 or in the range of about 10:1 to about 2000:1, or about 50:1 to about 500:1, or about 1400:1 to about 1500:1.

Although the atomizer is depicted as being disposed at the surface of fluid in the chamber, the assembly may be operated such that the atomizer is disposed above or below the surface of the fluid.

The embodiment of FIG. 2 comprises a primary tandem filter particle harvesting and collection system (left of drawing) and a secondary tandem filter particle harvesting and collection system (right of drawing). This equipment assembly is configured such that the particle harvesting and collection systems can be operated sequentially or simultaneously. Accordingly, the particle formation step can be conducted continuously or semi-continuously.

As depicted, the precipitation fluid milieu exits the chamber by way of an outlet (24) and directed to the left system by valve (26). Valve (28*a*) directs the milieu to harvesting filter (6*a*), whereby the solvent/anti-solvent mixture is separated from the particles (which are retained by the filter) and directed to a solvent separation vessel (7*a*). The solvent that is separated is conducted to the solvent collection vessel (8*a*). When charging of precipitation milieu into the harvesting filter is complete, the internal pressure thereof is reduced to below supercritical conditions. The valve (29*a*) is actuated and low pressure inert gas (from a supply 9*a*) is charged in reverse flow through the harvesting filter thereby dislodging particles retained by the filter to form a gaseous particle suspension. The valve (28*a*) is also actuated to direct the gaseous particle suspension to a collection filter (12*a*), which separates particles from the inert gas as described above. The separated particles are collected in the collection vessel (10*a*).

The secondary harvesting and collection system is configured and operated in much the same way as the primary one. For a continuous particle formation process, the valve (26) is toggled as needed from the primary system to the secondary system and back such that particle harvesting can occur in one system while particle collection occurs in the other system.

Figure 2:
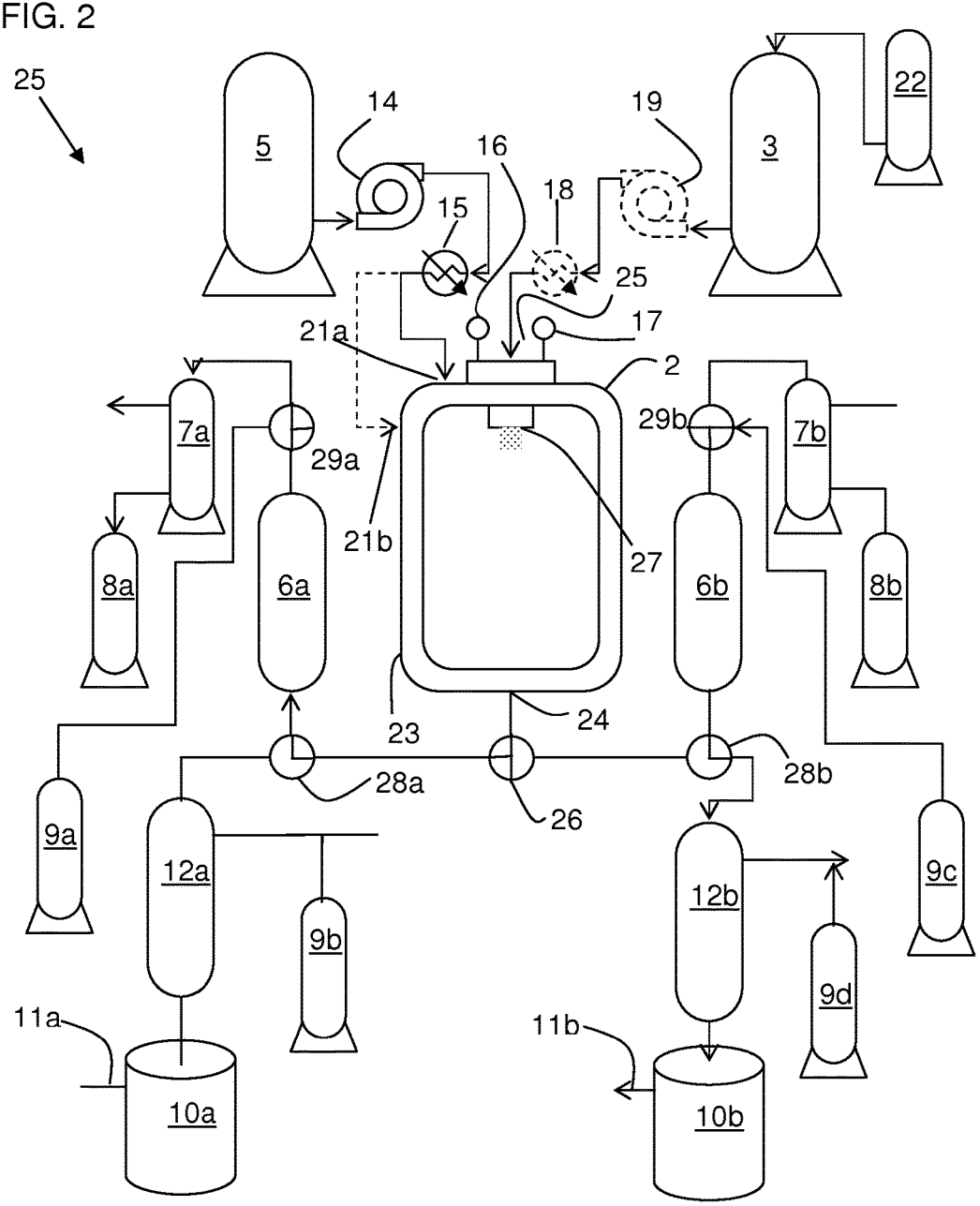
FIG. 2 depicts an alternate embodiment of the exemplary particle formation, separation and collection system (25) here comprising two exemplary tandem filter particle filtration systems arranged in parallel and configured for alternate or simultaneous operation.
Figure 3:
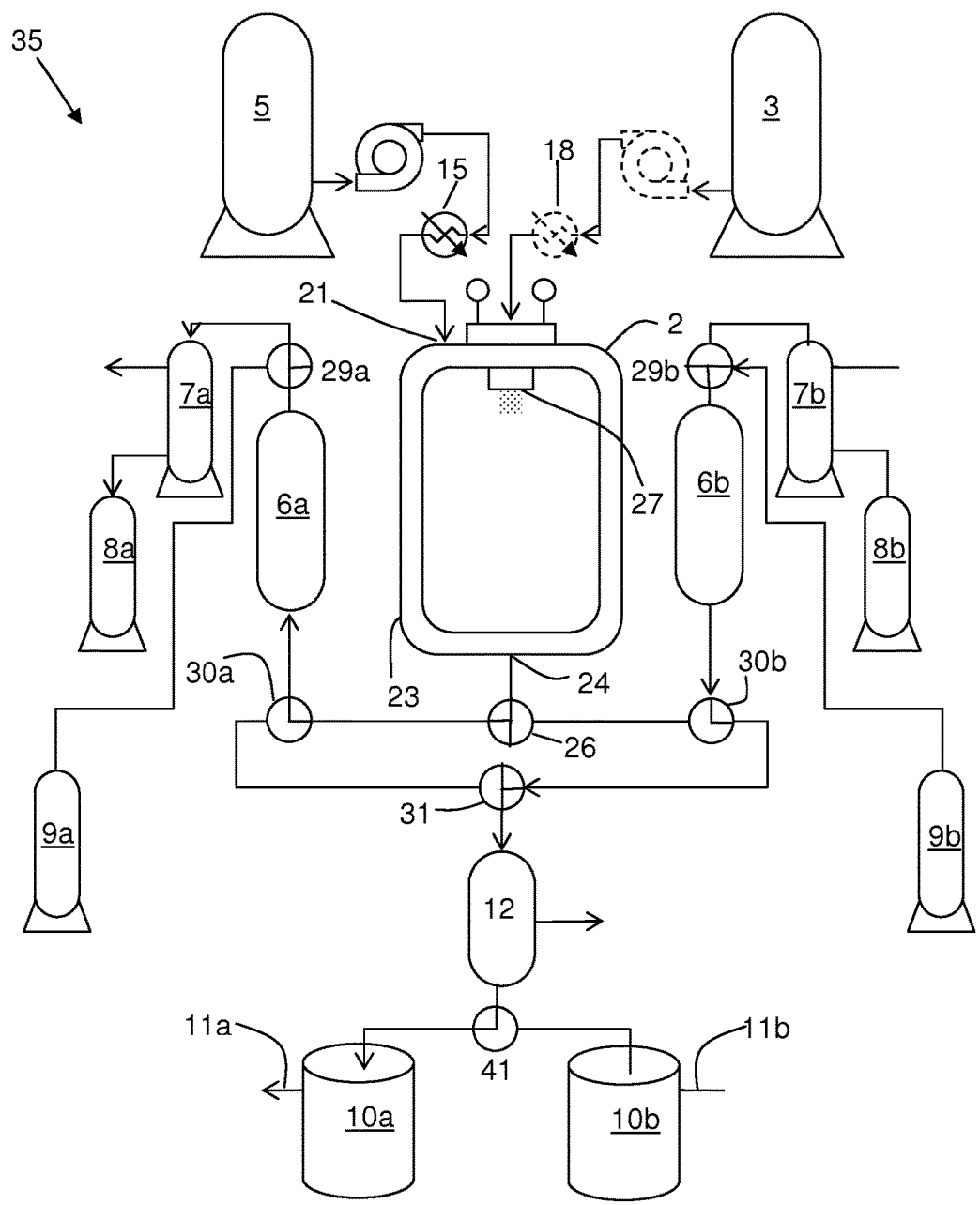
FIG. 3 depicts an alternate embodiment of the exemplary particle formation, separation and collection system (35) comprising an exemplary tandem filter particle filtration system and an additional harvesting filter arranged in parallel, wherein the two harvesting filters are arranged in parallel and are configured for simultaneous or alternate operation.

FIG. 3 depicts a schematic of an alternate equipment assembly (35) that can be used to prepare, harvest and collect particles. The particle formation system is very similar to that of FIG. 2, with the exception that the face of the atomizer is located below the surface or within the anti-solvent in the precipitation chamber. The assembly (35) also comprises a primary harvesting system and a secondary harvesting system similar to that of FIG. 2. A key difference between the assemblies (25) and (35) is that the redundancy of the collection system has been eliminated. Even though this assembly (35) is configured for continuous or semi-continuous particle formation and for simultaneous or sequential particle harvesting, it only employs a single collection filter. As depicted and due to the disposition of the valves (26, 29a and 30a), the primary harvesting system (on the left) is receiving precipitation milieu and separating particles from the solvent/anti-solvent mixture. The secondary harvesting system (on the right) is discharging and collecting particles due to disposition of the valves (29b, 30b and 31). Another key difference is that the collection system comprises two collection vessels (10a and 10b) and a valve (41) that alternately directs collected particles to one or the other of the vessels.

Figure 4:
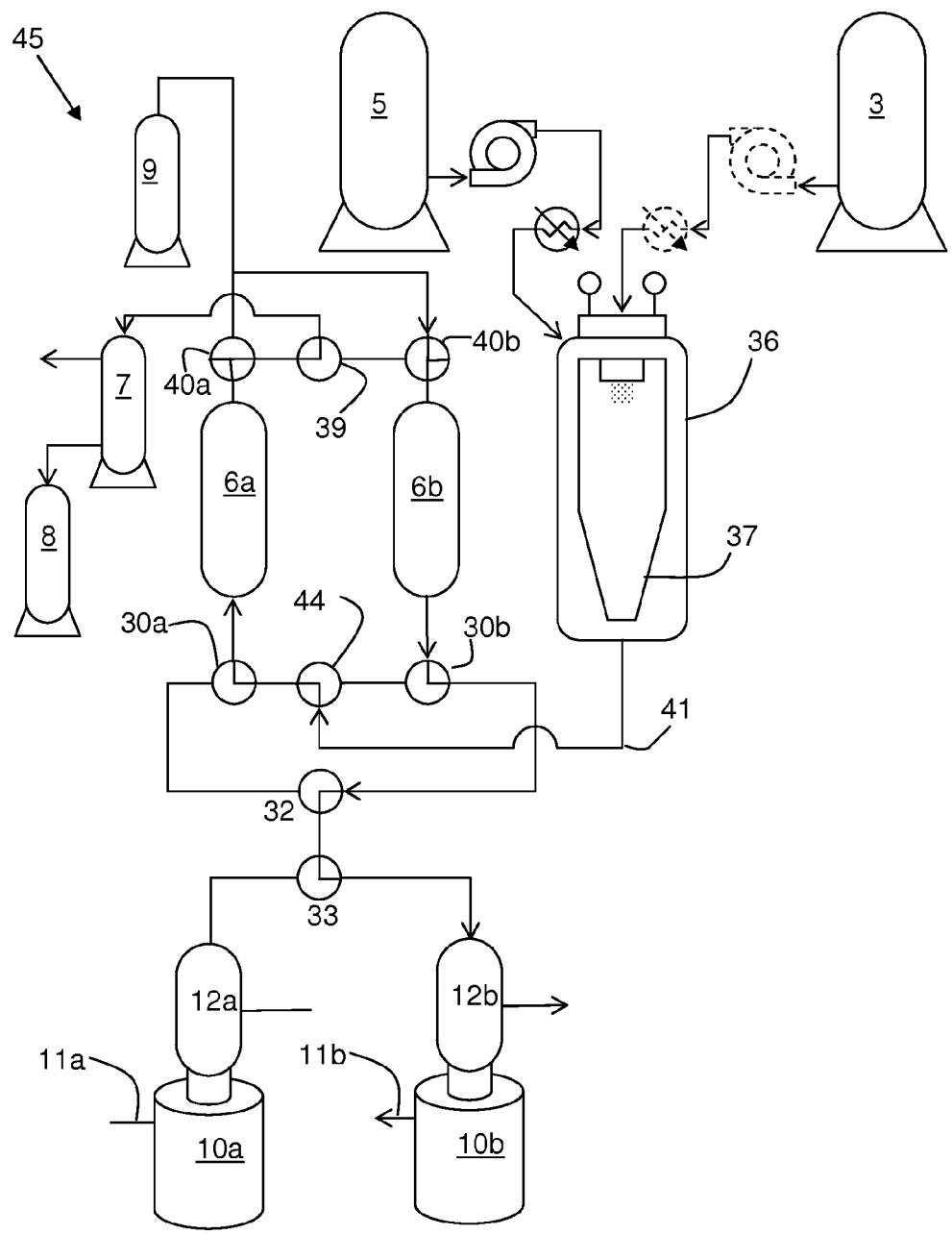
FIG. 4 depicts an alternate embodiment of the exemplary particle formation, separation and collection system (45) comprising two exemplary tandem filter particle filtration systems arranged in parallel and are configured for alternate operation.

FIG. 4 depicts a schematic of an alternate equipment assembly (45) that can be used to prepare, harvest and collect particles. The particle formation system is similar to that of FIG. 3, with the exception that some of the equipment redundancy has been removed. The assembly (45) comprises two tandem filter particle harvesting and collection systems arranged in parallel and configured to operate in sequence. A key difference between the assemblies (35) and (45) is that the redundancy of the solvent separation and solvent collection systems has been eliminated. This assembly (45) is configured for continuous or semi-continuous particle formation and for sequential particle harvesting and sequential particle collection. As depicted and due to the disposition of the valves (30a, 30b, 39, 40a and 44), the primary harvesting and collection system (6a, 12a on the left) is receiving precipitation milieu and separating particles from the solvent/anti-solvent mixture. The secondary harvesting system (6b, 12b on the right) is discharging and collecting particles due to disposition of the valves (30b, 40b, 39, 44, 32 and 33). Precipitation milieu is conducted (41) to valve (44) which directs the milieu to the harvesting filter (6a). The solvent/anti-solvent mixture is directed by valves (40a) and (39) to the solvent separation and collection system. While that process occurs, the particles already harvested by the harvesting filter (6b) are discharged. Gas is dispensed from a supply (9) and directed via a valve (40b) in reverse flow through the filter (6b). The gaseous particle suspension is directed by valves (30b, 32 and 33) to a collection filter (12b), whereby particles that are separated are forced by gravity into a vented (11b) collection vessel (10b). Operation between the primary and secondary harvesting and collection systems is affected simply by switching of the appropriate valves to direct flow of the process stream as required.

Another difference between the assemblies (35 and 45) is that the shape of the process cavity of the precipitation chamber has a tapered end to minimize accumulation of particles in the chamber after formation and facilitate cleaning of the chamber.

Figure 5:
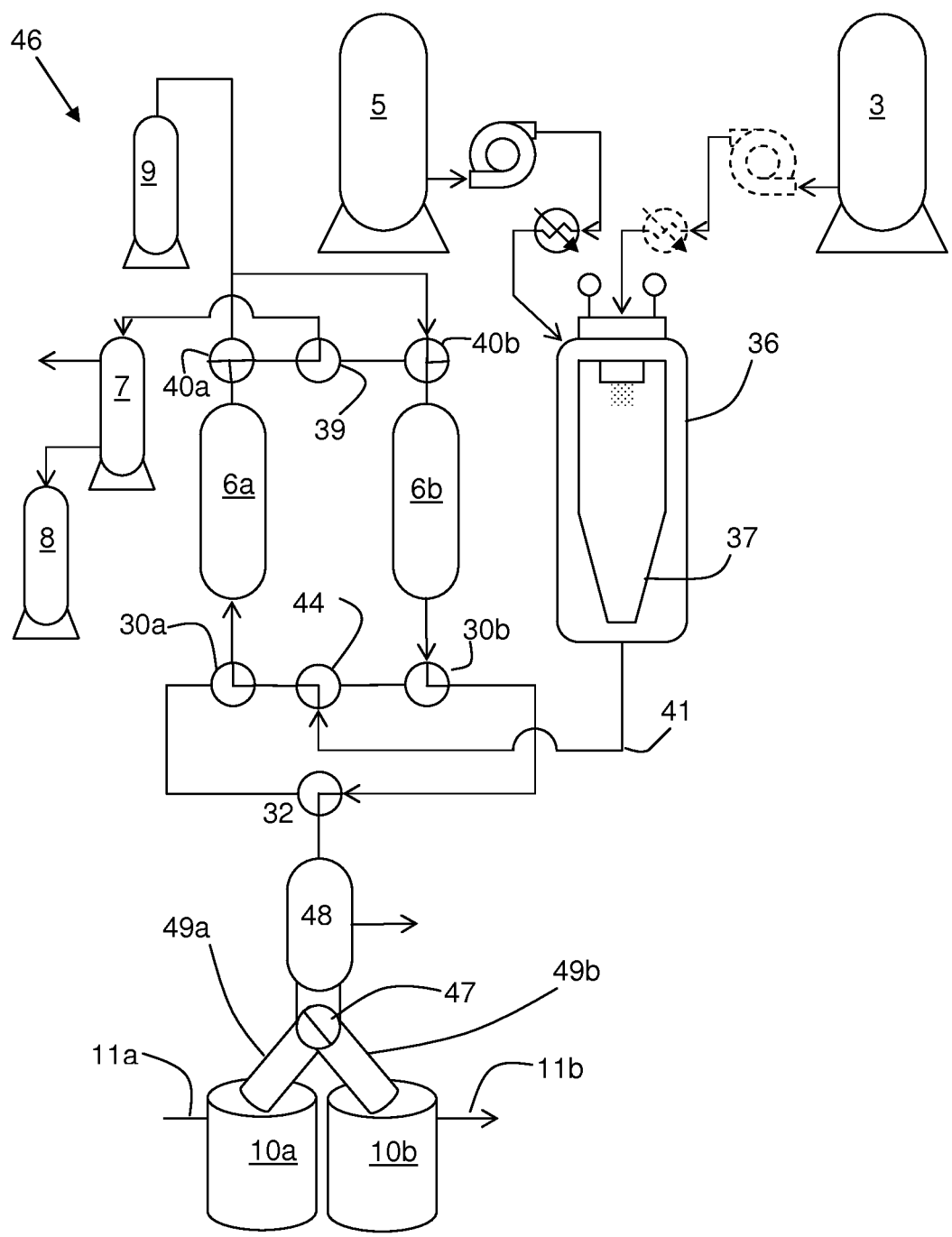
FIG. 5 depicts an alternate embodiment of the exemplary particle formation, separation and collection system (46) comprising two exemplary particle harvesting filters arranged in parallel and configured for alternate operation, one particle collection filter, and two collection vessels arranged in parallel and configured for alternate operation.

The equipment assembly (46) of FIG. 5 is similar in design to that of FIG. 4, with the exception that there is a single collection filter (48) that is engaged with two collection vessels. The valve (47) directs particles down a chute (49a, 49b) to a respective collection vessel. This equipment assembly is suitable for continuous operation by providing continuous particle formation, continuous particle harvesting with alternately operated parallel harvesting filters, and continuous particle collection with continuous particle collection filter operation and alternate filling of collection vessels.

Figure 6:
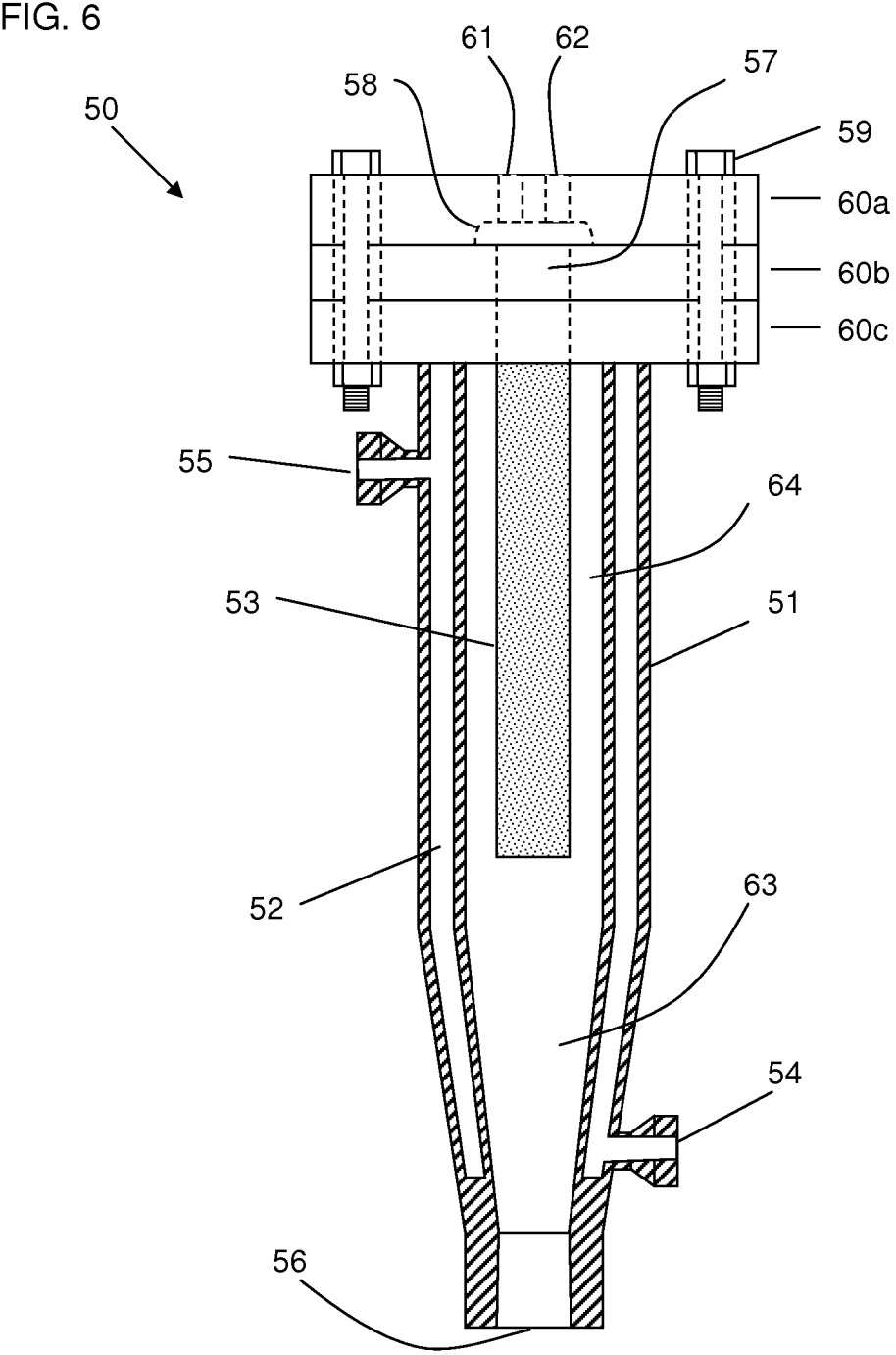
FIG. 6 depicts a partial cross-sectional side elevation view of an exemplary high pressure harvesting filter (50).

FIG. 6 depicts an exemplary harvesting filter (50) comprising an extended jacketed housing (51), an extended porous element (53) and a flanged (60a-60c) head. The interior surface of the housing defines an extended cylindrical upper section (64) and a downwardly-directed (downwardly pointing) tapered lower section (63) of a process cavity within which the porous element is disposed. The wall of the jacketed housing includes a cavity (52) within which temperature controlling material flows via ports (55) and (54). The process cavity includes an inlet (56) which also serves as an outlet when the filter is operated in the reverse direction as described herein. The flange (60b) of the head includes an outlet (57) which also serves as an inlet when the filter is operated in the reverse direction as described herein. The flange (60a) includes a cavity (58) and an inlet (61) and an outlet (62). A major portion or substantially all of the porous element can extend into the upper cylindrical portion. A minor or major portion of the porous element can extend into the inverted conical portion.

During forward operation, particles are retained by the porous element of the filter. Precipitation milieu enters the process cavity via the inlet (56), whereby solvent and anti-solvent pass through the porous element (not depicted in cross-section) to an internal conduit and are conducted to the outlet (57), the cavity (58), the outlet (62) and finally toward the solvent separation system (not depicted). The particles accumulate on the exterior surface of the porous element. In order to keep the temperature of the precipitation milieu within suitable operating range, temperature controlling fluid is conducted through the jacket.

In the reverse operation, particles are discharged from the filter. A gas is flowed through the inlet (61), the outlet (57, now serving as an inlet), the internal conduit of the porous element and through the porous element, thereby dislodging the particles and forming a gaseous particle suspension (particles entrained in a moving gas) that exits the housing via the inlet (56, now serving as an outlet).

Figure 7:
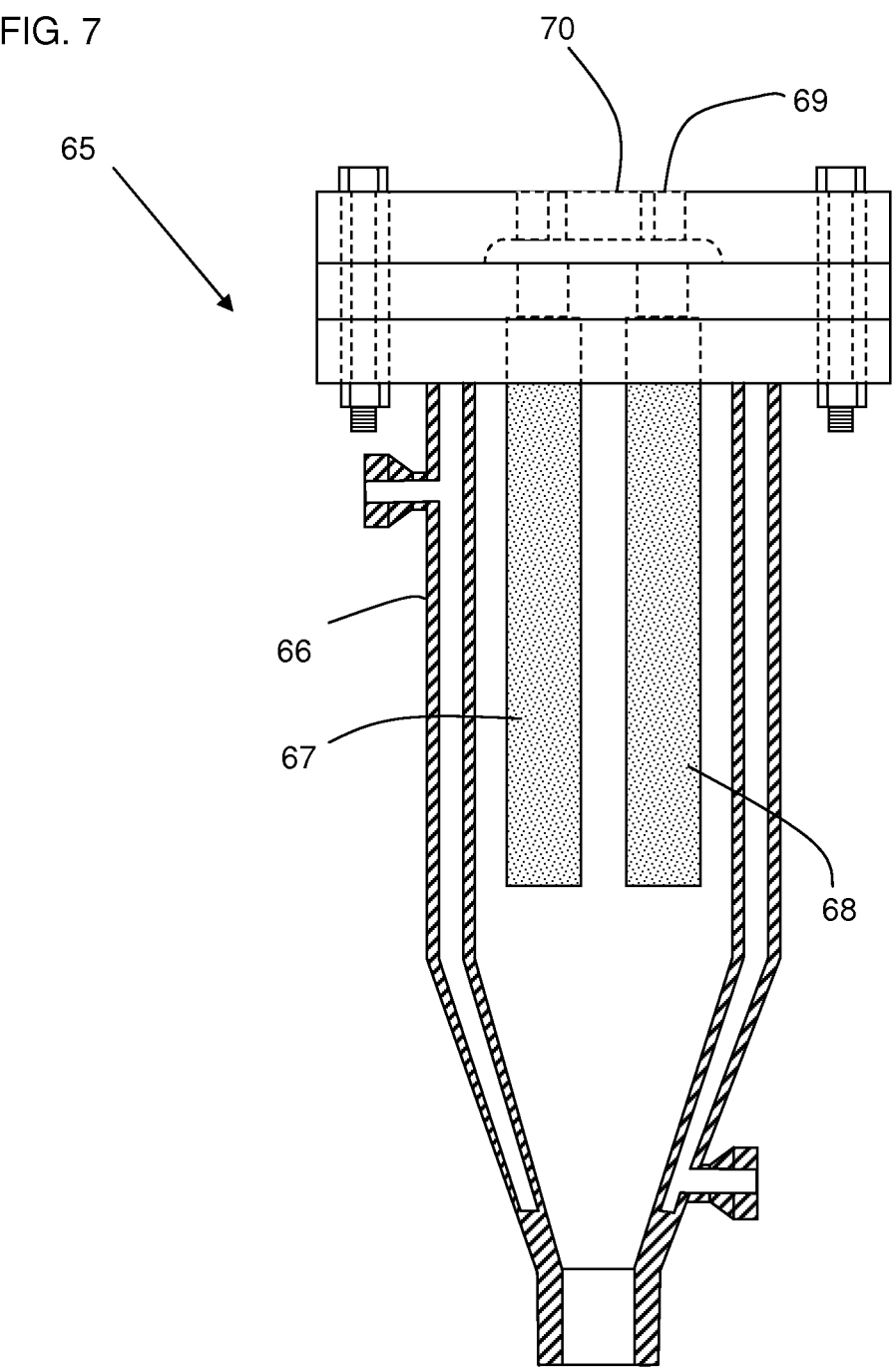
FIG. 7 depicts a partial cross-sectional side elevation view of another exemplary high pressure harvesting filter (65).

FIG. 7 depicts an alternate embodiment of a harvesting filter (65). It is similar in construction to the filter (50) of FIG. 6; however, this filter comprises two (67, 68; plural) extended porous elements disposed in the extended process cavity of the housing (60). The upper flange also comprises a single outlet (70) and two inlets (69); however, a single one of each or plural ones of each can also be used. Operation of this filter is the same as operation of the other harvesting filter.

Figure 8:
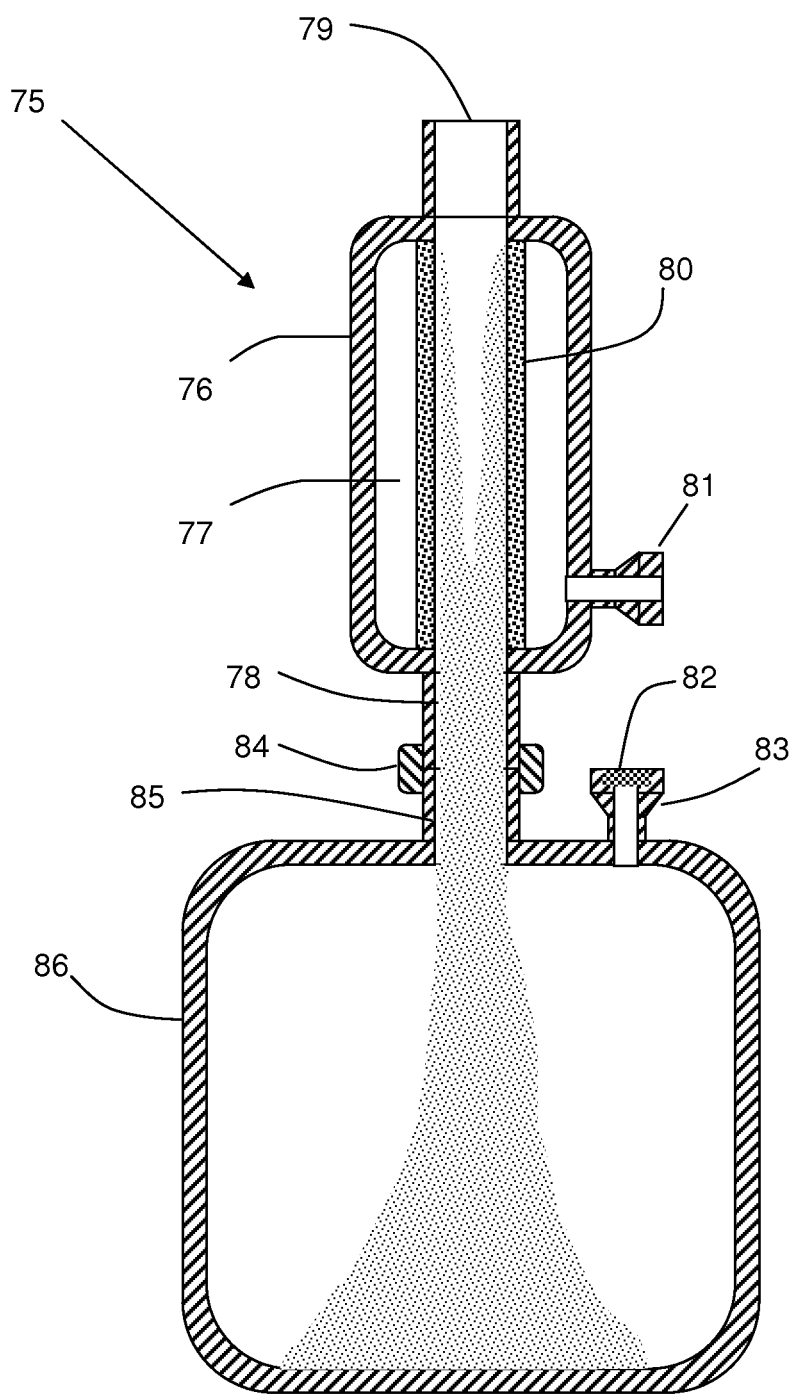
FIG. 8 depicts a cross-sectional side elevation view of an exemplary low pressure collection filter (77) in operation and connected to a collection vessel.

FIG. 8 depicts a collection filter (75) engaged with a collection vessel (86) via a coupling (84). The filter comprises a housing (76), an inlet (79), an outlet (78), an extended porous element (80) defining an internal conduit engaged with the inlet and outlet, a cavity (77) defined by the interior surface of the housing and the exterior surface of the porous element, and an outlet (81) in communication with and configured to release gas from the cavity (77). The collection vessel also comprises a vent (83) optionally comprising a filter, such as a frit, mesh, cloth or other such material (82)l. During operation, a gaseous particle suspension (particles entrained in a gas) enters the inlet (79) and is conducted through the internal conduit of the porous element, whereby gas passes through the porous element to the cavity (77) and out the outlet (81), but particles are retained within the internal conduit and drop through the outlet (78), the inlet (85) and accumulate in the collection vessel (86). The vent (83) only allows a minor portion of the gas to exit, since the majority of the gas in the suspension is removed by way of the outlet (81).

Although not depicted in FIG. 8, an inert gas source that pulses gas in a reverse process direction through the outlet (81) can be included to dislodge any particles that might accumulate at the surface of the porous element, even though such accumulation should be minimal.

FIG. 9 depicts a cross-sectional side view of a closed tube-shaped porous element (90) comprising an open end (93) of an interior lumen, a closed end (94), an outer porous portion (lamina) having a coarse porosity, and an inner porous portion (lamina) having a fine porosity. The porous element (100) of FIG. 10 is substantially the same as that of FIG. 9 except that the fine porosity portion is at the exterior and the coarse porosity portion is at the interior of the porous element.

FIG. 11A depicts a partial sectional side view of a filter assembly (107) comprising a housing (106) with a tapered, slanted or conical lower portion and a single tube shaped porous element (105) as depicted in FIG. 9 having a coarse porosity outer surface. During the first part of the harvesting operation, process fluid is charged into the housing in the direction of the lower darkened arrow and filtrate exits the housing in the direction of the upper darkened arrow, whereby particles are retained on the outer surface of the porous element and within the process cavity of the filter. During the second part of the harvesting operation, gas is charged into the housing in the direction of the upper white arrow and a gaseous suspension of particles exits the housing in the direction of the lower white arrow, thereby discharging the particles from the housing.

The filter assembly (101) of FIG. 11B is similar to that of FIG. 11A except that the porous element (108) possesses a larger outer diameter, and optionally of greater length, than the porous element (105) and thereby occupies a greater percentage of the interior cavity of the housing. The filter assembly (102) of FIG. 11C is similar to that of FIG. 11A except that it comprises two porous elements. The filter assembly (103) of FIG. 11D is similar to that of FIG. 11A except that it comprises three porous elements. The filter assembly (104) of FIG. 11E is similar to that of FIG. 11D except that the porous elements are upside down and engaged with a plate at the lower end of the housing such that process fluid contacts the interior of the porous element and particles are retained within the interior of the porous elements rather than at their exterior.

FIGS. 12A-12E are similar to FIGS. 11A-11E, respectively, except that the porous element of FIG. 10 is used, such that the smaller porosity lamina is at the exterior and the coarser porosity lamina is at the interior.

FIG. 13 depicts a porous element (120) in the shape of a flat plate. It comprises a coarse porosity lamina (121) and fine porosity lamina (122). The porous element can be mounted in a filter assembly such that process fluid contacts the coarse lamina or the fine lamina. The plate can be flat or curved.

FIG. 14A depicts a partial sectional view of a filter assembly (125) comprising a housing (127) and a porous element (126) having a fine porosity lamina that contacts process fluid and a coarse porosity lamina through which filtrate passes. During the first part of the harvesting operation, process fluid is charged into the housing in the direction of the lower darkened arrow and filtrate exits the housing in the direction of the upper darkened arrow, whereby particles are retained on the outer surface of the porous element and within the process cavity of the filter. During the second part of the harvesting operation, gas is charged into the housing in the direction of the upper white arrow and a gaseous suspension of particles exits the housing in the direction of the lower white arrow, thereby discharging the particles from the housing.

FIG. 14B depicts a filter assembly similar to that of FIG. 14A except that the porous element of FIG. 14B is inverted such that a coarse porosity lamina contacts process fluid and filtrate passes through a fine porosity lamina.

FIGS. 15A and 15B are similar to FIGS. 14A and 14B, respectively, except that the housing is much shorter in length.

FIG. 16A depicts a partial sectional side view of a filter (135) comprising the plate shaped porous element (136) of FIG. 13 within a round housing (spherical, elliptical, cylindrical). The upper and lower portions of the housing can be substantially of the same shape, size and/or volume. During the first part of the harvesting operation, process fluid is charged into the housing in the direction of the lower darkened arrow and contacts the fine porosity portion of the porous element, whereby filtrate passes through the coarse porosity portion and exits the housing in the direction of the upper darkened arrow, whereby particles are retained on the outer surface of the porous element and within the process cavity of the filter. During the second part of the harvesting operation, gas is charged into the housing in the direction of the upper white arrow and a gaseous suspension of particles exits the housing in the direction of the lower white arrow, thereby discharging the particles from the housing. The filter can be inverted such that process fluid contacts the coarse porosity portion first.

FIG. 16B depicts a partial sectional side view of a filter (137) similar to the filter of FIG. 16A except that the body is square, rectangular or cylindrical. This filter can also be inverted during operation.

FIG. 17A depicts a partial sectional side view of a filter (140) comprising a housing (141) and porous element (142). Unlike the filter of FIG. 14A, wherein the porous element (126) is mounted perpendicular to the lengthwise axis of the housing and to the flow or process fluid through the housing, the porous element (142) is mounted at a non-perpendicular angle with respect to the lengthwise axis of the housing or with respect to the flow of process fluid through the housing. In this embodiment, the process fluid contacts the fine porosity lamina. In the alternate embodiment of FIG. 17B, the process fluid contacts the coarse porosity lamina.

As used herein, the term "downstream" is with respect to the flow of the gaseous particle suspension. For example, when the collection system receives the gaseous particle suspension from the harvesting filter system, the collection system is considered to be downstream of the harvesting filter system. Likewise, when the collection filter system receives the gaseous particle suspension from the harvesting filter system, the collection filter system is considered to be downstream of the harvesting filter system.

In some embodiments, the particle collection system, which is a low pressure system, is integrated with the collection filter system. The collection filter can be engaged with and downstream of the collection system. FIG. 18 depicts part of the filtration and collection systems downstream of the particle formation system. The harvesting filter system (150) is disposed above and conductively engaged, via the valve (153) and optional tubing (conduit), with the particle inlet (154) of the collection system (152). The collection filter (151) is disposed above the collection system and is engaged with the gas outlet (155) of the collection system (152). A portion of the collection filter (151) is optionally disposed within the collection system. In embodiments such as this, the collection system is thus disposed (in terms of process flow) between the harvesting filter and the collection filter of a tandem filtration system. The collection system can comprise a second outlet (156) to serve as a vent and/or sampling tube.

The invention thus provides a filtration and collection equipment assembly wherein the systems thereof are conductively engaged in the following sequential process order: high pressure harvesting filter system engaged with low pressure collection system which is engaged with low pressure collection filter system. In other words, the invention provides a particle filtration and collection equipment assembly comprising a tandem filtration system and a collection system, wherein: a) the tandem filtration system comprises a high-pressure filter system and a low pressure filter system; and b) the collection system is conductively engaged between the high pressure filter system and the low pressure filter system.

Figure 18:
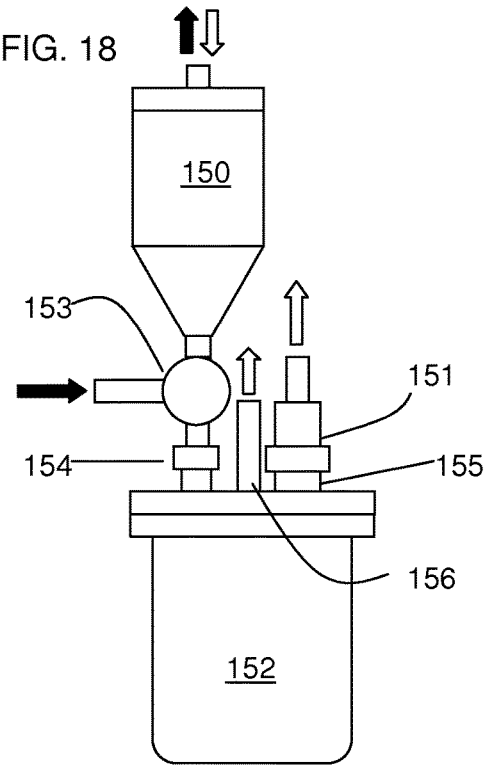
FIG. 18 depicts a side elevation view of a partial equipment assembly having a high pressure harvesting filter system, low pressure particle collection system and low pressure collection filter system in that order.
Figure 19:
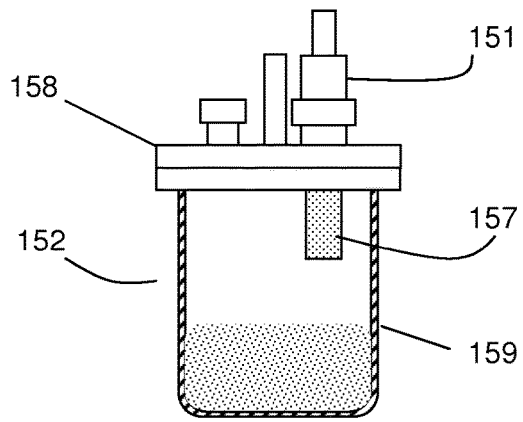
FIG. 19 depicts a partial sectional side elevation view of the particle collection system and collection filter system of FIG. 18.
Figure 20:
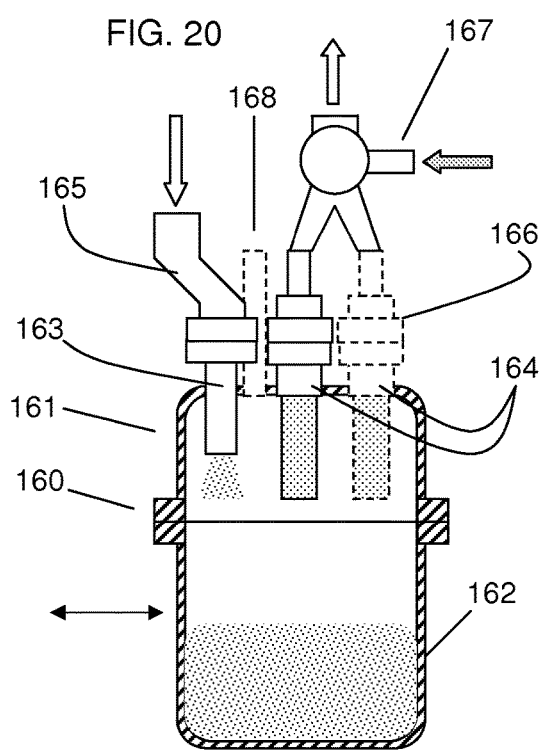
FIG. 20 depicts a partial sectional side elevation view of an alternate embodiment of the particle collection systems and collection filter systems of FIGS. 18 and 19.
Figure 21:
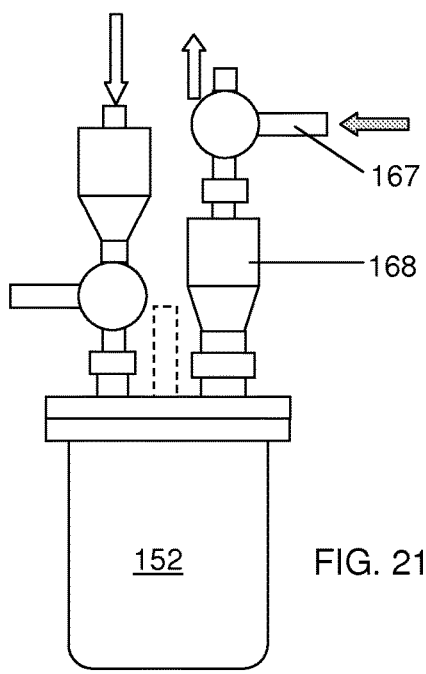
FIG. 21 depicts a side elevation view of an alternate embodiment of the particle collection system and collection filter system of FIG. 18.

The assembly of FIG. 18 employs a process for a tandem filtration system and collection system as follows: a) high pressure filtration of a supercritical fluid or near supercritical fluid particle suspension in a first process direction (black arrows) through a high pressure harvesting filter; b) pressure reduction of the atmosphere within harvesting filter; c) flow of low pressure gas in an opposite second process direction (white arrows, wherein direction of flow is with respect to flow through the filtration medium of the harvesting filter) through the harvesting filter to form a gaseous particle suspension which is conducted into a collection system via an inlet thereof; and d) low pressure filtration of the gaseous particle suspension with a collection filter engaged with a gas outlet of the collection system, whereby particles are retained within and accumulate within the collection system.

In some embodiments, the filtration and collection systems of the process comprises the following steps: a) filtering a supercritical fluid or near supercritical fluid particle suspension in a first process direction (black arrows) through a high pressure harvesting filter; b) reducing the pressure of the atmosphere within harvesting filter; c) flowing a low pressure gas in an opposite second process direction (white arrows) through the harvesting filter to form a gaseous particle suspension which is conducted into a collection system via a particle inlet thereof; and d) filtering the low pressure gaseous particle suspension with a collection filter engaged with a gas outlet of the collection system, thereby retaining and collecting particles within the collection system.

In embodiments wherein the collection system is between (with respect to process flow) the harvesting filter and the collection filter, the majority, or all, of the gas from the gaseous particle suspension flows through the at least one collection filter.

FIG. 19 depicts an embodiment of the invention wherein a low pressure collection filter (151) includes a porous element (157) that extends into the collection system (152). The collection system comprises a header (158, cover) and a collection vessel (159), which are detachable from one another. In this case, the porous element has an open end (93) and a closed end (94), for example as depicted in FIGS. 9 and 10. The porous element comprises a lumen (conduit) defined by filtration media. The porous element can be sintered or fritted or can be a cloth or mesh or wound fiber or as otherwise described herein. The porous element can be a flat or curved plate, e.g. as depicted in FIG. 13.

FIG. 20 depicts an alternate embodiment of the partial equipment assembly of FIG. 19. The collection system (160) comprises an extended header (161, cover) and a collection vessel (162) that are detachable from one another and together form a receptacle (cavity) for particles that are collected. The header comprises at least one particle inlet (163) and at least one gas outlet (164). The particle inlet is engaged with a horizontally offset conduit (165) that conducts the gaseous particle suspension (from the harvesting filter system) into the collection system. The at least one gas outlet (164) is engaged with at least one collection filter system (166) (two depicted, with an optional one depicted in dashed lines). The majority or all of the gas that enters the collection system exits through the least one gas outlet having the collection filter system. After collection of particles therein, the collection vessel (162) can be disengaged from the extended head permit (161) and replaced with another collection vessel. An optional vent (168) (and/or sampling port) is depicted in dashed lines. The collection filter system can further comprise a gas inlet (167) used to back-flush (direction of grey arrow) the filtration medium of the collection filter(s), thereby removing (dislodging) any particles that have accumulated on its exposed surface within the collection vessel. The dislodged particles will be retained in the collection vessel.

As used herein, the term "back-flush" refers to flow of gas in an opposite (reverse) second direction through process equipment. For example, gas passes through the filtration medium of the collection filter in a forward first process direction when particles are separated from gas in the gaseous particle suspension. Gas can then be passed in a reverse direction (back-flush) through the filtration medium to dislodge particles that have accumulated on the surface of the filtration medium.

FIG. 21 depicts an alternate embodiment of the partial equipment assembly of FIG. 18. In this embodiment, the collection filter (168) is engaged with and disposed above the gas outlet of the collection system; however, the porous element (filtration medium) of the collection filter is not disposed within the cavity defined by the header and vessel of the collection system. Any particles that accumulate at the surface of the porous element can be dislodged there from by back-flushing the porous element with gas from the gas inlet (167) such that the loose particles fall back into the collection vessel through its gas outlet port.

In some embodiments, the invention provides a particle formation and collection system comprising in process order sequence: a particle formation system, a high pressure harvesting filter system, a collection system and a low pressure filter system. The particle formation system comprises a particle formation system that forms a supercritical or near-supercritical fluid (liquid) particle suspension. The high pressure harvesting filter receives and filters the fluid particle suspension in a first process direction and then forms a low pressure gaseous particle suspension in an opposite second process direction, wherein the process direction is with respect to direction through a porous element in the filter. The collection system receives the gaseous particle suspension and collects the particles therein. The collection filter separates particles from gas in the gaseous particle suspension and retains the particles within the collection system while permitting passage of the gas through the filter. The harvesting filter is directly or indirectly engaged with an inlet of the collection system.

The collection filter is directly or indirectly engaged with a gas outlet of the collection system. At least a portion of or the entire length of porous element of the collection filter can be disposed within the collection system.

In order to establish the importance of the differences between this instant equipment assembly employing a tandem filter system as described herein and other filter assemblies, operation of the assembly was compared to another system excluding the harvesting filter and employing a precipitation vessel, a collection filter and a vented collection vessel. The following observations were made: a) particles blew out of the vent of the collection vessel when the harvesting filter was back-flushed with low pressure nitrogen; b) particles accumulated at and adhered to the interior surface of the lid and of the upper portion of the collection vessel. However, when a collection filter was employed downstream of the harvesting filter, particles were cleanly and easily collected in the bottom of the collection vessel and the particles did not adhere to the interior surface of the collection vessel.

In order to establish the importance of back-flushing of the harvesting filter with a low pressure gas, the harvesting filter was operated with and without back-flushing. Without back-flushing, a substantial amount of particles accumulated on the surface of the porous element and at the bottom of the process cavity. The particles had to be dislodged from the porous element and removed from the bottom by physical/mechanical means. With back-flusing, no accumulation of particles at the bottom of the cavity was observed and only minimal accumulation of the particles on the surface of the porous element was observed.

The process fluid comprises at least one solvent and at least one solute dissolved therein. The process fluid can comprise two or more or plural solvents. The concentration of solute in the process fluid can be varied as needed. In some embodiments, the concentration is at least about 0.1% wt and can range from 0.1% to about 20% wt.

The dimensions of the housing defining the precipitation chamber can be varied as desired. Although the housing is depicted as being vertically disposed, it can be slanted or horizontally disposed. The housing (and thus the chamber) can be longer than its width, can have the same width and length or can be shorter than its width. A narrow housing defining a narrow chamber can be used. In some embodiments, the lengthwise axis of the chamber is vertical and the diameter of the chamber is shorter than its length.

Even though the system is particularly suitable for supercritical fluid applications, it can also be employed to prepare particles from non-critical and near-critical anti-solvent/solvent particle formation systems, wherein the process fluid (solute-containing solvent) is atomized into or onto anti-solvent.

The solute can be any compound or combination of compounds or materials that is poorly soluble or insoluble in the anti-solvent. Suitable compounds include a pharmaceutical active ingredient, pharmaceutical excipients (inactive ingredient), chemical, natural product, biologic compound, pesticide, herbicide, or other chemical. For example, an active pharmaceutical ingredient may be mixed with a polymer such as PLGA and co-precipitated as a complex with unique properties distinct from the active pharmaceutical ingredient alone. Similarly, two pharmaceutically active ingredients could be mixed together in a single solvent and co-precipitated to produce a combination drug product.

The process fluid and/or the anti-solvent can comprise one or more additional ingredients that are ultimately incorporated into the particles and/or onto the surface of the particles.

As used herein, the term solvent refers to a fluid that dissolves a solute to form a solute-containing fluid (process fluid). The solvent must also be soluble in or miscible with an anti-solvent such that placing a solute-containing solvent into the anti-solvent will result in precipitation of the solute to form particles. The solvent is typically an organic solvent. Suitable organic solvents include ethanol, methanol, 1-propanol, isopropanol, 1-butanol, 2-butanol, tert-butanol, acetone, methylethylketone, dichloromethane, chloroform, hexafluoroisopropanol, diethyl ether, dimethylamide, dimethylformamide, DMSO and mixtures thereof.

As used herein, the term anti-solvent refers to a liquid (or compressed gas or plasma or supercritical fluid) in which the solute that forms the particles is poorly soluble or insoluble. The anti-solvent can serve as a solvent for and can be used to remove unwanted components in the particles. The anti-solvent can be capable of forming a supercritical fluid. Suitable supercritical fluid-forming anti-solvents can comprise carbon dioxide, propane, butane, isobutane, nitrous oxide, sulfur hexafluoride and trifluoromethane.

Various different solvent/anti-solvent combinations can be used. Selection of a particular combination will depend upon the degree of solubility of the solvent within the solvent and the anti-solvent.

A porous element can comprise one or more frits, one or more rings, one or more porous plates, one or more porous tubes or a combination thereof. The porous element can comprise a sintered metal, ceramic, TEFLON®, plastic, steel and other such materials. In some embodiments, the porous element comprises at least one sintered metal tube. The average (or nominal) pore size of porous element will be at least 10%, at least 15%, at least 20%, at least 40%, at least 50%, at least 75%, at least 80%, at least 90%, at least 95% or at least 99% smaller than the average diameter of particles to be processed by the filter. The transverse (perpendicular to the lengthwise axis) cross-section of the porous element can be any geometrical shape. In some embodiments, the transverse cross-section comprises a circle, oval, octagon, pentagon, hexagon or other geometric shape. In some embodiments, the transverse cross-section of the porous element comprises substantially the same shape as the transverse cross-section of the upper cylindrical portion of the process cavity defined by the housing.

The housing of a filter can be adapted for vertical installation into an equipment assembly. In some embodiments, the lower port of the housing is disposed at or adjacent the lower end of the cavity, and the upper port is disposed at or adjacent the upper end of the process cavity. In a filter, the porous element can be installed vertically within the housing such that it is disposed above the inlet port and beneath the outlet port of the housing.

A temperature controller can be exterior to, interior to or integral with a housing. In some embodiments, the temperature controller jackets the housing. It can comprise at least one heating element, at least one cooling element or a combination thereof. The jacket can comprise a fluid-filled cavity. In some embodiments, the housing comprises an interior wall defining the process cavity and an exterior wall spaced away from the interior wall, wherein the walls and the space there between together define a temperature-controlling jacket.

By "downwardly-pointing" conical portion is meant a conical section of the cavity wherein the narrower diameter portion of the cone is below the wider diameter portion of the cone. In other words, the conical portion of the cavity is defined by a tapered (at least with respect to its inner diameter) section of the housing, thereby providing the conical portion with a funnel shape. The cross-sectional geometry of the surface defining the conical section can be as desired. In some embodiments, the conical portion has a circular or oval cross-section when observed perpendicular to the lengthwise axis of the conical portion.

In view of the above description and the examples below, one of ordinary skill in the art will be able to practice the invention as claimed without undue experimentation. The foregoing will be better understood with reference to the following examples that detail certain assemblies and methods according to the present invention. All references made to these examples are for the purposes of illustration. The following examples should not be considered exhaustive, but merely illustrative of only a few of the many embodiments contemplated by the present invention.

EXAMPLE 1

The following process can be used to make particles comprising acetaminophen. The following ingredients in the amounts indicated are used.

| INGREDIENT | AMOUNT (% WT.) |
| --- | --- |
| Acetone | 96.5 |
| acetaminophen | 3.5 |

An equipment assembly as depicted in FIG. 5 is employed. A process fluid is prepared by dissolving acetaminophen in acetone in amounts according to the table above. Dissolution can be done while heating and/or mixing. The anti-solvent is supercritical carbon dioxide ($scCO_2$).

The precipitation chamber is charged with $scCO_2$ and its temperature and pressure are equilibrated. The pressure is about 1,200 psi and the temperature is about 38° C. Flow of $scCO_2$ through the precipitation chamber is initiated. Clean solvent is conducted through an atomizer, comprising a vibrating porous mesh and a capillary nozzle upstream of the mesh, by way of an inlet in the precipitation chamber, whereby it is atomized directly into the $scCO_2$. The flow rate (about 730 ml/min) of $scCO_2$ into the chamber exceeds flow rate of solvent and process fluid (about 10 ml/min) into the chamber. The feed stream is gradually changed from clean solvent to process fluid. The process fluid is conducted through a capillary tube to contact the back-side of the vibrating porous mesh, whereby it is atomized directly into the $scCO_2$. The process can be operated without the vibrating mesh and the process fluid would flow directly from the capillary tube into the $scCO_2$. Formation of particles occurs as droplets of process fluid contact the $scCO_2$ and solvent in the process fluid diffuses into the $scCO_2$ and causes precipitation of the solute into particles.

A high pressure particle harvesting filter is equilibrated with $scCO_2$ which is run through the filter in anticipation of loading of the precipitation milieu. Following formation of the particles in the precipitation chamber, the precipitation fluid milieu (comprising $scCO_2$, solvent and particles) is conducted through an outlet toward the opposite end (with respect to the inlet) of the chamber to a particle collection filter, wherein the fluid $scCO_2$ and solvent are separated from the particles at the surface of the porous element in the filter. The $scCO_2$ and solvent are conducted to a solvent separation vessel where the pressure is about 200 psi, which causes separation of solvent from anti-solvent by changing the anti-solvent from supercritical to gas phase. From there, the separated solvent is conducted to a solvent collection vessel. While the particles reside in the harvesting filter, additional clean $scCO_2$ is flowed through the filter to remove solvent from the particles. The pressure within the filter is reduced.

The particles are then discharged from the harvesting filter by providing a low pressure (about 10 to about 100 psi, about 20 to about 50 psi, or about 30 to about 40 psi) reverse flow of gas, e.g. nitrogen, across the porous element to dislodge the particles from the porous element. The gas can be pulsed through the porous element. The dislodged particles are conducted as a gaseous particle suspension to a particle collection filter, whereby gas passes through the porous element and particles fall into a vented collection vessel.

EXAMPLE 2

The following process can be used to make particles comprising paclitaxel and PLGA (poly-(lactic acid)-co-(glycolic acid) polymer). The following ingredients in the amounts indicated are used.

| INGREDIENT | AMOUNT (% WT.) |
| --- | --- |
| Acetone | 96 |
| Paclitaxel | 2.5 |
| PLGA | 1.5 |

The process of Example 1 is followed with the following exceptions.

The process fluid is prepared by dissolving paclitaxel and PLGA in acetone in amounts according to the table above.

EXAMPLE 3

The following process can be used to make particles comprising meloxicam. The following ingredients in the amounts indicated are used.

| INGREDIENT | AMOUNT (% WT.) |
| --- | --- |
| Acetone:DMF 20:80 | 96.8 |
| meloxicam | 3.2 |

An equipment assembly as depicted in FIG. 5 is employed. A process fluid is prepared by dissolving meloxicam in acetone/dimethylformamide (20:80) in amounts according to the table above. Dissolution can be done while heating and/or mixing. The anti-solvent is supercritical carbon dioxide ($scCO_2$).

The precipitation chamber is charged with $scCO_2$ and its temperature and pressure are equilibrated. The pressure is about 1,200 psi and the temperature is about 38° C. Flow of $scCO_2$ through the precipitation chamber is initiated. Clean solvent is conducted through an atomizer, comprising a vibrating porous mesh and a capillary nozzle upstream of the mesh, by way of an inlet in the precipitation chamber, whereby it is atomized directly into the $scCO_2$. The flow rate (about 730 ml/min) of $scCO_2$ into the chamber exceeds flow rate of solvent and process fluid (about 10 ml/min) into the chamber. The feed stream is gradually changed from clean solvent to process fluid. The process fluid is conducted through a capillary tube to contact the back-side of the vibrating porous mesh, whereby it is atomized directly into the $scCO_2$. The process can be operated without the vibrating mesh and the process fluid would flow directly from the capillary tube into the $scCO_2$. Formation of particles occurs as droplets of process fluid contact the $scCO_2$ and solvent in the process fluid diffuses into the $scCO_2$ and causes precipitation of the solute into particles.

A high pressure particle harvesting filter is equilibrated with $scCO_2$ which is run through the filter in anticipation of loading of the precipitation milieu. Following formation of the particles in the precipitation chamber, the precipitation fluid milieu (comprising $scCO_2$, solvent and particles) is conducted through an outlet toward the opposite end (with respect to the inlet) of the chamber to a particle harvesting filter, wherein the fluid $scCO_2$ and solvent are separated from the particles at the surface of the porous element in the filter. The $scCO_2$ and solvent are conducted to a solvent separation vessel where the pressure is about 200 psi, which causes separation of solvent from anti-solvent by changing the anti-solvent from supercritical to gas phase. From there, the separated solvent is conducted to a solvent collection vessel. While the particles reside in the harvesting filter, additional clean $scCO_2$ is flowed through the filter to remove solvent from the particles. The pressure within the filter is reduced resulting in a phase change of the carbon dioxide from fluid to gaseous.

The particles are then discharged from the harvesting filter by providing a low pressure (about 10 to about 100 psi, about 20 to about 50 psi, or about 30 to about 40 psi) reverse flow of gas, e.g. nitrogen, across the porous element to dislodge the particles from the porous element. The gas can be pulsed through the porous element. The dislodged particles are conducted as a gaseous particle suspension to a particle collection filter, whereby gas passes through the porous element and particles fall into a vented collection vessel.

EXAMPLE 4

The following process can be used to make particles comprising biosynthetic human insulin. The following ingredients in the amounts indicated are used.

| INGREDIENT | AMOUNT (% WT.) |
| --- | --- |
| 1,1,1,3,3,3-hexafluoro-2-propanol | 97 |
| insulin | 3.0 |

An equipment assembly as depicted in FIG. 5 is employed. A process fluid is prepared by dissolving human biosynthetic insulin in 1,1,1,3,3,3-hexafluoro-2-propanol (HFIP) in amounts according to the table above. Dissolution can be done while heating and/or mixing. The anti-solvent is supercritical carbon dioxide ($scCO_2$).

The precipitation chamber is charged with $scCO_2$ and its temperature and pressure are equilibrated. The pressure is about 1,200 psi and the temperature is about 38° C. Flow of $scCO_2$ through the precipitation chamber is initiated. Clean solvent is conducted through an atomizer, comprising a vibrating porous mesh and a capillary nozzle upstream of the mesh, by way of an inlet in the precipitation chamber, whereby it is atomized directly into the $scCO_2$. The flow rate (about 730 ml/min) of $scCO_2$ into the chamber exceeds flow rate of solvent and process fluid (about 10 ml/min) into the chamber. The feed stream is gradually changed from clean solvent to process fluid. The process fluid is conducted through a capillary tube to contact the back-side of the vibrating porous mesh, whereby it is atomized directly into the $scCO_2$. The process can be operated without the vibrating mesh and the process fluid would flow directly from the capillary tube into the $scCO_2$. Formation of particles occurs as droplets of process fluid contact the $scCO_2$ and solvent in the process fluid diffuses into the $scCO_2$ and causes precipitation of the solute into particles.

A high pressure particle harvesting filter is equilibrated with $scCO_2$ which is run through the filter in anticipation of loading of the precipitation milieu. Following formation of the particles in the precipitation chamber, the precipitation fluid milieu (comprising $scCO_2$, solvent and particles) is conducted through an outlet toward the opposite end (with respect to the inlet) of the chamber to a particle harvesting filter, wherein the fluid $scCO_2$ and solvent are separated from the particles at the surface of the porous element in the filter. The $scCO_2$ and solvent are conducted to a solvent separation vessel where the pressure is about 200 psi, which causes separation of solvent from anti-solvent by changing the anti-solvent from supercritical to gas phase. From there, the separated solvent is conducted to a solvent collection vessel. While the particles reside in the harvesting filter, additional clean $scCO_2$ is flowed through the filter to remove solvent from the particles. The pressure within the filter is reduced resulting in a phase change of the carbon dioxide from fluid to gaseous.

The particles are then discharged from the harvesting filter by providing a low pressure (about 10 to about 100 psi, about 20 to about 50 psi, or about 30 to about 40 psi) reverse flow of gas, e.g. nitrogen, across the porous element to dislodge the particles from the porous element. The gas can be pulsed through the porous element. The dislodged particles are conducted as a gaseous particle suspension to a particle collection filter, whereby gas passes through the porous element and particles fall into a vented collection vessel.

EXAMPLE 5

The following process can be used to make particles comprising Bovine Serum Albumin (BSA). The following ingredients in the amounts indicated are used.

| INGREDIENT | AMOUNT (% WT.) |
|---|---|
| 1,1,1,3,3,3-hexafluoro-2-propanol (HFIP) | 97.5 |
| BSA | 2.5 |

An equipment assembly as depicted in FIG. 5 is employed and a process similar to that of Example 4 is employed. A process fluid is prepared by dissolving human BSA in 1,1,1,3,3,3-hexafluoro-2-propanol (HFIP) in amounts according to the table above. Dissolution can be done while heating and/or mixing. The anti-solvent is supercritical carbon dioxide ($scCO_2$).

EXAMPLE 6

The following process can be used to make particles comprising docetaxel. The following ingredients in the amounts indicated are used.

| INGREDIENT | AMOUNT (% WT.) |
|---|---|
| acetone | 96.5 |
| docetaxel | 3.5 |

An equipment assembly as depicted in FIG. 5 is employed, and a process similar to that of Example 3 is employed. A process fluid is prepared by dissolving docetaxel in acetone in amounts according to the table above. Dissolution can be done while heating and/or mixing. The anti-solvent is supercritical carbon dioxide ($scCO_2$).

EXAMPLE 7

The following process can be used to make particles comprising dexamethasone. The following ingredients in the amounts indicated are used.

| INGREDIENT | AMOUNT (% WT.) |
|---|---|
| ethanol | 98.5 |
| dexamethasone | 1.5 |

An equipment assembly as depicted in FIG. 5 is employed, and a process similar to that of Example 3 is employed. A process fluid is prepared by dissolving dexamethasone in ethanol in amounts according to the table above. Dissolution can be done while heating and/or mixing. The anti-solvent is supercritical carbon dioxide ($scCO_2$).

EXAMPLE 8

The following process can be used to make particles comprising paliperidone. The following ingredients in the amounts indicated are used.

| INGREDIENT | AMOUNT (% WT.) |
|---|---|
| DCM:MeOH (30:70) | 97.23 |
| paliperidone | 2.77 |

An equipment assembly as depicted in FIG. 5 is employed, and a process similar to that of Example 3 is employed. A process fluid is prepared by dissolving paliperidone in DCM:MeOH in amounts according to the table above. Dissolution can be done while heating and/or mixing. The anti-solvent is supercritical carbon dioxide ($scCO_2$).

As used herein, the term about is taken to mean ±10%, ±5%, ±2.5% or ±1% of a respective value.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A particle formation and collection equipment assembly comprising:
 a) a high pressure particle formation system that forms a particle-containing high pressure liquid suspension;
 b) at least one high pressure harvesting filter system that receives and filters the particle-containing high pressure liquid suspension, wherein the high pressure particle harvesting filter system comprises:
  a high pressure housing defining a lengthwise process cavity comprising a downwardly-pointing conical portion, at least one inlet port and at least one outlet port;
  a liquid particle suspension supply line engaged with the inlet port and configured to provide a high pressure liquid particle suspension comprising particles and anti-solvent;
  a gas supply line engaged with the outlet port and configured to provide a low-pressure inert gas;
  a temperature controller for controlling the temperature of the housing; and
  at least one lengthwise porous element extending into the cavity and comprising a porous wall defining a lengthwise inner conduit engaged with the at least one outlet port,
  wherein,
  the porous element is engaged directly or indirectly with the outlet port;
  the filter system is configured to receive high pressure particle suspension in a first forward process direction and to receive a low pressure inert gas in a second reverse process direction, wherein process direction is with respect to flow through the porous element;
 c) at least one collection vessel system, downstream of the harvesting filter, that receives the particle-containing low pressure gaseous suspension from the harvesting filter and collects particles; and
 d) at least one low pressure collection filter system, conductively engaged with and downstream of the at least one collection vessel, that separates gas from particles in the particle-containing low pressure gaseous suspension and retains particles in the collection vessel.

2. The equipment assembly of claim 1 further comprising: a) one or more temperature controllers for one or more of the precipitation chamber, collection filter, emptying filter and collection vessel; b) one or more valves; c) one or more actuators; d) one or more back pressure regulators; d) one or more flow controllers; e) a gas pulsing system configured to pulse gas into at least the harvesting filter; f) one or more computers having a memory storage medium containing software or logic adapted to control operation of one or more components of the system; g) one or more pressure sensors; h) one or more valves that direct flow of a liquid particle suspension to the harvesting filter and direct flow of a gaseous particle suspension from the harvesting filter to the collection filter; i) one or more pumps; j) one or more temperature sensors; k) one or more SCF supply systems; l) one or more process fluid supply systems; m) one or more pumps for pumping process fluid, supercritical carbon dioxide ($scCO_2$) or a combination of process fluid and $scCO_2$; n) one or more solvent separation vessels; o) one or more solvent collection vessels; and/or p) one or more in-line sensors.

3. The equipment assembly of claim 2 comprising at least one temperature controller, at least one temperature sensor, at least one pressure sensor, at least one back pressure regulator, at least one flow controller, at least one valve, at least one SCF supply system and at least one process fluid supply system.

4. The equipment assembly of claim 2, wherein an in-line sensor is independently selected at each occurrence from the group consisting of spectrophotometric sensor, particle size sensor, pressure sensor, temperature sensor, infrared sensor, near-infrared sensor, and ultraviolet sensor.

5. The equipment assembly of claim 1 wherein the disperser comprises: a) a vibratable member; b) a vibrator comprising at least one piezoelectric component; c) a converging or diverging nozzle that generates a standing ultrasonic wave during operation; d) a conduit for process fluid and a conduit for SCF; e) a capillary nozzle; and/or f) a vibrator and vibratable member.

6. The equipment assembly of claim 5, wherein the vibratable member is a nozzle, plate or mesh.

7. The equipment assembly of claim 1, wherein, for the harvesting filter: a) the process cavity is vertically oriented along its lengthwise axis; b) at least one inlet port is configured to serve as an outlet port for a gaseous particle suspension; c) the porous element and the housing are cylindrical; d) the temperature controller comprises a heating and/or cooling jacket surrounding the housing; e) the geometry of the conical portion is such that the upper wider end has a diameter of about 25 to about 125 mm, the lower narrower end has a diameter of about 5 to about 50 mm and the conical portion is about 50 to about 250 mm in length; f) the process cavity further comprises a linear cylindrical portion in which the porous element is disposed; g) the spacing between the outer surface of the porous element and the inner surface of the process cavity is in the range of about 5 to about 100 mm; h) the outlet port is configured as reversible-flow port to serve as an outlet for liquid and an inlet for gas; i) the diameter of the inner conduit is in the range of about 5 to about 60 mm; j) the outer diameter of the porous element is in the range of about 10 to about 60 mm; k) the system further comprises one or more valves that direct flow of a liquid particle suspension to the harvesting filter and direct flow of a gaseous particle suspension from the harvesting filter; l) the high pressure filter and precipitation chamber are adapted to operate at about 800 to about 3000 psi; m) a portion of the process cavity of the filter housing is cylindrical, rectangular, ellipsoidal or spherical; n) the porous element is disposed within the process cavity such that its surface is tangential to, perpendicular to or at a non-perpendicular angle with respect to the linear axis of the housing or with respect to the overall flow of fluid across or through the surface of the porous element; o) the porous element comprises substantially the same porosity throughout; p) the porous element comprises a first porous portion and a second porous portion, wherein the average diameter of the pores of the first portion is greater than the average diameter of the pores of the second portion; q) the porous element comprises two substantially coextensive porous portions differing in the average diameter of their respective pores; r) a first porous portion of the porous element has an average pore diameter of about 0.3-0.6 microns, and a second porous portion of the porous element has an average pore diameter of about 0.02-0.10 microns; s) the porous element can be a tube or plate; t) a portion of the porous element is a lamina and the porous element comprises two or more laminas; u) the high pressure filter comprises one, two, three, four or plural porous elements; v) the porous element is conductively engage with the upper portion of the filter assembly; w) the porous element is conductively engaged with the lower portion of the filter assembly; x) one or more porous elements together occupy up to about 90% of the volume of the process cavity of the filter assembly; and/or y) the filter housing and/or porous element is invertible.

8. The equipment assembly of claim 7, wherein the vertical orientation is perpendicular to the ground or parallel to the linear axis of a plumb bob line.

9. The equipment assembly of claim 1, wherein the low pressure particle collection filter system comprises:

a low pressure housing defining a lengthwise process cavity and comprising at least one inlet port, at least one gas outlet port and at least one particle outlet port; and a gaseous particle suspension supply line engaged with the at least one inlet and configured to provide a low pressure gaseous particle suspension comprising particles and gas;

at least one lengthwise porous element extending into the cavity and comprising a porous wall defining a lengthwise inner conduit engaged with the at least one inlet port and the at least one particle outlet port;

wherein, the filter system is configured to receive low pressure gaseous particle suspension in a forward process direction;

the porous element is configured to retain particles and allow passage of gas to the at least one gas outlet;

the conduit of the porous element is oriented such that particles fall via gravity through the at least one particle outlet port.

10. The equipment assembly of claim 9, wherein for the collection filter: a) the inner conduit is vertically oriented along its lengthwise axis; b) at least one inlet port is configured to receive a gaseous particle suspension; c) the porous element is cylindrical; d) the inner conduit of the porous element has an inner diameter in the range of about 5 to about 60 mm; e) the system further comprises a gas pulsing system configured to pulse gas in a reverse operations direction from the gas outlet of the housing to the porous element; and/or f) the collection vessel is disposed beneath the porous element or at a level below the porous element.

11. The equipment assembly of claim 10, wherein the vertical orientation is perpendicular to the ground or parallel to the linear axis of a plumb bob line.

12. The equipment assembly of claim 1, wherein the equipment assembly comprises: a) two particle harvesting filters, two particle collection filters and two collection vessels; b) two particle harvesting filters, one particle collection filter and one or more collection vessels; c) two particle harvesting filters, two particle collection filters and one or more collection vessels; d) two particle harvesting filters, one particle collection filter and one or more collection vessels; e) two tandem filter particle harvesting and collection systems arranged in parallel; f) two or more particle harvesting filters arranged in parallel, one particle collection filter and two or more collection vessels arranged in parallel; g) two or more precipitation chambers; h) at least two tandem filter particle filtration systems configured to operate alternately or simultaneously; and/or i) at least two collection systems configured to operate alternately or simultaneously.

13. The equipment assembly of claim 1, wherein the collection system or collection vessel is vented or comprises an outlet port for gas.

14. The equipment assembly of claim 13, wherein the vent comprises filtration medium.

15. The equipment assembly of claim 1 further comprising:

a) a SCF supply system; and b) a process fluid supply system.

16. The equipment assembly of claim 1, wherein the at least one low pressure collection filter system comprises a housing defining a process cavity, and at least one porous element.

17. The equipment assembly of claim 16, wherein the housing of the low pressure collection filter system further comprises at least one outlet port disposed at a level below the porous element.

18. The equipment assembly of claim 17, wherein the porous element of the low pressure collection filter system extends into the process cavity and comprises a porous wall defining a lengthwise inner conduit.

19. The equipment assembly of claim 1, wherein the at least one collection vessel system, downstream of the harvesting filter, comprises at least one gas outlet and at least one particle inlet that receives the particle-containing low pressure gaseous suspension from the harvesting filter and retains particles in the collection vessel; and the at least one low pressure collection filter system, conductively engaged with the at least one gas outlet and downstream of the at least one collection vessel, separates gas from particles in the particle-containing low pressure gaseous suspension and retains particles in the collection vessel.

20. The equipment assembly of claim 1, wherein: 1) a majority of gas exits the collection system through one or more gas outlets engaged with one or more collection filters; 2) the collection system comprises at least one collection vessel and at least one removable header, at least one particle inlet, and at least one gas outlet; 3) the collection filter and harvesting filter are disposed above the collection system; 4) at least a portion of filtration medium of the collection filter is disposed within a cavity defined by the header and collection vessel; 5) the collection system further comprises at least one vent and/or at least one sampling port; 6) the collection filter comprises at least one porous element that extends into the collection system, wherein the porous element comprises a lumen defined by filtration media, wherein the conduit has a closed end and an open end; 7) the collection system comprises a header and a collection vessel that are detachable from one another; 8) the collection system comprises an extended header and a collection vessel that are detachable from one another and together form a receptacle for particles that are collected; 9) the particle inlet of the collection system is engaged with a horizontally offset conduit that conducts the gaseous particle suspension from the harvesting filter system into the collection system; 10) the collection vessel is removable; 11) the collection filter system further comprises a gas inlet for gas used to back-flush the filtration medium of the collection filter(s), thereby dislodging any particles that have accumulated on its exposed surface within the collection vessel; and/or 12) the collection filter system further comprises a gas inlet used to back-flush gas through filtration medium of the collection filter.

21. The particle formation and collection equipment assembly of claim 20, wherein: a) the porous element can be sintered or fritted or can be a cloth or mesh or wound fiber; b) the porous element is a flat or curved plate; and/or c) the collection filter is engaged with and disposed above the gas outlet of the collection system and the porous element of the collection filter is not disposed within the cavity defined by the header and vessel of the collection system.

22. A process for filtering and collecting particles from a supercritical fluid or near-supercritical fluid particle suspension, the process employing the equipment assembly of claim 1 and the process comprising:

a) filtering the supercritical fluid or near supercritical fluid particle suspension in a first process direction through the at least one high pressure harvesting filter;

b) reducing the pressure of the atmosphere within the at least one high pressure harvesting filter;

c) flowing a low pressure gas in an opposite second process direction through the at least one high pressure harvesting filter to form a gaseous particle suspension which is conducted into the at least one collection vessel system via a particle inlet thereof; and d) filtering the low pressure gaseous particle suspension with the at least one low pressure collection filter system engaged with a gas outlet of the at least one collection vessel system, thereby retaining and collecting particles within the at least one collection vessel system.

* * * * *